US008679840B2

(12) United States Patent
Schendel et al.

(10) Patent No.: US 8,679,840 B2
(45) Date of Patent: Mar. 25, 2014

(54) COMPOSITIONS FOR THE PREPARATION OF MATURE DENDRITIC CELLS

(75) Inventors: Dolores J. Schendel, Munich (DE); Anke Zobywalski, Griesheim (DE); Iris Bigalke, Neuried (DE)

(73) Assignee: Helmholtz Zentrum München Deutsches Forschungszentrym für Gesundheit und Umwelt (Gmbh), Neuherberg (DE)

( * ) Notice: Subject to any disclaimer, the term of this patent is extended or adjusted under 35 U.S.C. 154(b) by 594 days.

(21) Appl. No.: 12/294,453

(22) PCT Filed: Mar. 28, 2007

(86) PCT No.: PCT/EP2007/002773
§ 371 (c)(1),
(2), (4) Date: Aug. 2, 2010

(87) PCT Pub. No.: WO2007/110240
PCT Pub. Date: Oct. 4, 2007

(65) Prior Publication Data
US 2010/0284976 A1 Nov. 11, 2010

Related U.S. Application Data

(60) Provisional application No. 60/825,822, filed on Sep. 15, 2006.

(30) Foreign Application Priority Data

Mar. 28, 2006 (EP) ..................................... 06006373

(51) Int. Cl.
C12N 5/071 (2010.01)
C12N 5/00 (2006.01)
C12N 5/02 (2006.01)

(52) U.S. Cl.
USPC .......................................... 435/372; 435/377

(58) Field of Classification Search
None
See application file for complete search history.

(56) References Cited

FOREIGN PATENT DOCUMENTS

WO    WO 00/47719    8/2000

OTHER PUBLICATIONS

Wesa et al., 2001, Int. Immunol. vol. 13: 1053-1061.*
Rubio et al., 2005, Int. Immunol. vol. 17: 1561-1572.*
Hochrein et al., "Differential Production of IL-12, IFN-α and IFN-γ by Mouse Dendritic Cell Subsets," *Journal of Immunology*, 166:5448-5455, 2001.
Ahn et al., "IL-4 is more effective than IL-13 for in vitro differentiation of dendritic cells from peripheral blood mononuclear cells," *Int. Immunol.*, 17(10):1337-46, 2005.
Banchereau et al., "Dendritic cells as therapeutic vaccines against cancer," *Nat. Rev. Immunol.*, 5(4):296-306, 2005.
Becker et al., "Adoptive tumor therapy with T lymphocytes enriched through an IFN-γ capture assay," *Nat. Med.*, 7:1159-1162, 2001.
Berger et al., "Efficient elutriation of moncytes within a closed system (Elutra) for clinical-scale generation of dendritic cells," *J. Immunol. Methods.*, 298(1-2):61-72, 2005, Erratum in: *Immunol Methods.*, (1-2):152, 2005.
Campbell et al., "Isolation and generation of clinical-grade dendritic cells using the CliniMACS system," *Methods Mol. Med.*, 109:55-70, 2005.
Dieckmann et al., "Optimizing the exogenous antigen loading of mono-cyte derived dendritic cells," *Int. Immunol.*, 17(5):621-35, 2005.
Dubsky et al., "Human dendritic cell subsets for vaccination," *J. Clin. Immunol.*, 25(6):551-72, 2005.
Engleman et al., "Inductuion of immunity to tumor-associated antigens following dendritic cell vaccination of cancer patients" *Clin. Immunol.*, 106(1):10-5, 2003.
Escudier et al., "Vaccination of metastatic melanoma patients with autologous dendritic cell (DC) derived-exosomes: results of the first phase I clinical trial," *J. Transl. Med.*, 3:(10):1-13, 2005.
Figdor et al., "Dendritic cell immunotherapy: mapping the way," *Nat. Med.*, 10(5):475-80, 2004.
Frankenberger et al., "Cell-based vaccines for metastatic renal cell carcinoma: genetically-engineered tumor cells and monocyte-derived cells," *World J. Urol.*, 3:166-174, 2005.
Garrone et al., "Fas ligation induces apoptosis of CD40-activated human B lymphocytes," *J. Exp. Med.*, 182:1265-73, 1995.
Gautier et al., A type I interferon autocrine-paracrine loop is involved in toll-like receptor-induced interleukin-12p70 secretion by dendritic cells, *J. Exp. Med.*, 201(9):1435-46, 2005.
Gong et al., "Induction of anti-leukemic cytotoxic T lymphocytes by fusion of patient-derived dendritic cells with autologous mycoblasts," *Leuk. Res.*, 28(12):1303-12, 2004.
Griffioen et al., "Analysis of T-cell responses in metastatic melanoma patients vaccinated with dendritic cells pulsed with tumor lysates," *Cancer Immunol. Immunother.*, 53(8):715-22, 2004.
Grunebach et al., "Cotransfection of dendritic cells with RNA coding for HER-2/neu and 4-1BBL increases the induction of tumor antigen specific cytotoxic T lymphocytes," *Cancer Gene Ther.*, 12(9)::749-56, 2005.
Javorovic et al., "RNA transfer by electroporation into mature dendritic cells leading to reactivation of effector-memory cytotoxic T lymphocytes: A quantitative analysis," *Mol. Ther.*, 12:734-743, 2005.
Jonuleit et al., "Cytokines and their effects on maturation, differentiation and migration of dendritic cells," *Archives of Dermatological Research*, 289(1):1-8, 1996.
Jonuleit et al., "Pro-inflammatory cytokines and prostaglandins induce maturation of potent immunostimulatory dendritic cells under fetal calf serum-free conditions," *European Journal of Immunology*, 27(12):3135-3142, 1997.
Kato et al., "Differential roles of MDA5 and RIG-I helicases in the recognition of RNA viruses," *Nature*, 441:101-105, 2006.

(Continued)

Primary Examiner — Amy Juedes
(74) Attorney, Agent, or Firm — Parker Highlander PLLC

(57) ABSTRACT

The invention relates to a method for in vitro maturation of at least one immature dendritic cell, comprising stimulating said immature dendritic cell with TNFα, IL-1β, IFNγ, a TLR7/8 agonist and prostaglandin E2 (PG). Furthermore, the invention relates to a composition comprising these factors as well as to mature dendritic cells produced by a method of the invention.

18 Claims, 9 Drawing Sheets

(56) References Cited

OTHER PUBLICATIONS

Figure 1:
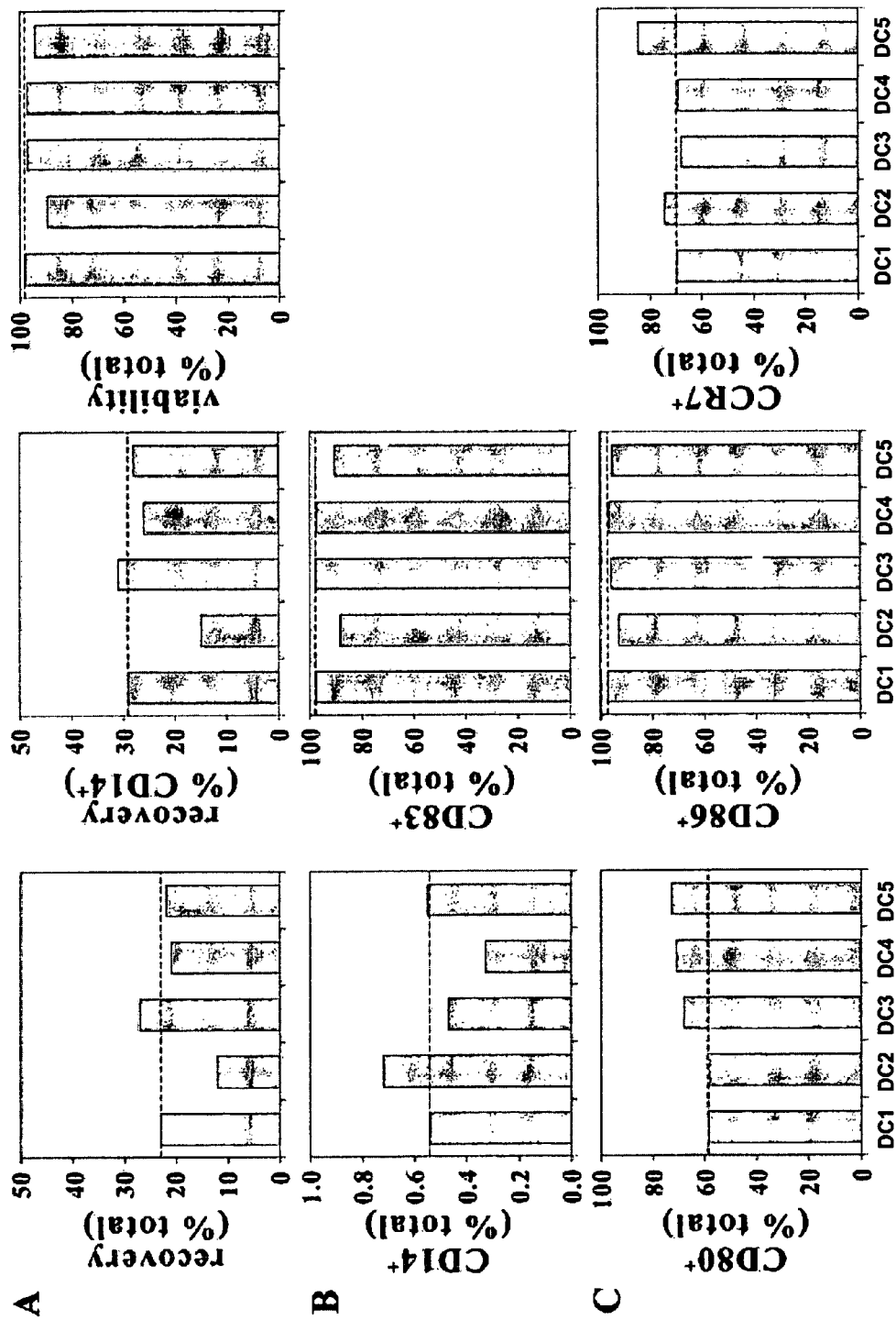

Kawamura et al., "Dendritic cells that endocytosed antigen-containing IgG-liposomes elicit effective antitumor immunity," *J. Immunother.*, 29(2):165-74, 2006.

Kikuchi et al., "Vaccination of glioma patients with fusions of dendritic and glioma cells and recombinant human interleukin 12," *J. Immunother.*, 27(6):452-9, 2004.

Kyte et al., "Preclinical full-scale evaluation of dendritic cells transfected with autologous tumor-mRNA for melanoma vaccination," *Cancer Gene Ther.*, 12(6):579-91, 2005.

Langenkamp et al., "Kinetics of dendritic cell activation: impact on priming of TH1, TH2 and nonpolarized T cells," *Nat. Immunol.*, 1(4):311-6, 2000.

Lanzavecchia et al., "Regulation of T cell immunity by dendritic cells," *Cell*, 106:263-266, 2001.

Mailliard et al., "Alpha-type 1 polarized dendritic cells: A novel immunization tool with optimized CTL-inducing activity," *Cancer Res.*, 64(17):5934-7, 2004.

Mosca et al., "A subset of human monocyte-derived dendritic cells expresses high levels of interleukin-12 in response to combined Cd40 ligand and interferon-gamma treatment," *Blood.*, 96(10):3499-504, 2000.

Muller et al., "Fetal calf serum-free generation of functionally active murine dendritic cells suitable for in vivo therapeutic approaches," *The Journal of Investigative Dermatology*, 114(1):142-148, 2000.

Nair et al., "Induction of primary carcinembyronic antigen (CEA)-specific cytotosic T lymphocytes in vitro using human dendritic cells transfected with with RNA," *Nat. Biotechnol.*, 16:364-369, 1998.

Napolitani et al., "Selected toll-like receptor agonist combinations synergistically trigger a T helper type 1-polarizing program in dendritic cells," *Nat. Immunol.*, 6(8):769-76, 2005.

Navabi et al., "Preparation of human ovarian cancer ascites-derived exosomes for a clinical trial," *Blood Cells Mol. Dis.*, 35(2):149-52, 2005.

O'Garra, "Cytokines induce the development of functionally heterogeneous T helper cell subsets," *Immunity*, 8:275-283, 1998.

Peng et al., "Generation and maturation of dendritic cells for clinical applications under serum free conditions," *J. Immunother.*, 28(6):599-609, 2005.

Pohla et al., "Allogeneic vaccination for renal cell carcinoma: development and monitoring," *Bone Marrow Transplant*, 25:83-87, 2000.

Rengaragjan et al., "Transcriptional regulation of Th1/Th2 polarization," *Immunol. Today*, 21(10):479-83, 2000.

Salcedo et al., "Vaccination of melanoma patients using dendritic cells loaded with an allogeneic tumor cell lysate," *Cancer Immunol. Immunother.*, 55:819-829, 2006.

Schuler et al., "The use of dendritic cells in cancer immunotherapy," *Curr. Opin. Immunol.*, 15(2):138-147, 2003.

Strasser et al., "Comparison of two apheresis systems for the collection of CD14+ cells intended to be used in dendritic cell culture," *Transfusion*, 43(9):1309-16, 2003, Erratum in *Transfusion*, 43(10):1502, 2003.

Su et al., "Telomerase mRNA-transfected dendritic cells stimulate antigen-specific CD8+ and CD4+ T cell responses in patents with metastatic prostate cancer," *J. Immunol.*, 174(6):3798-807, 2005.

Weeratna et al., "TLR agonists as vaccine adjuvants: Comparison of CpG ODN and Resiquimod (R-848)," *Vaccine*, 23(45):5263-5270, 2005.

Zobywalski et al., "Generation of clinical grade dendritic cells with capacity to produce biologically active IL-12p70," *J Transl Med.*, 5:18, 2007.

Jongmans et al., "Th1-polarizing capacity of clinical-grade dendritic cells is triggered by ribomunyl but is compromised by $PGE_2$," *J Immunother*, 28(5):480-487, 2005.

\* cited by examiner

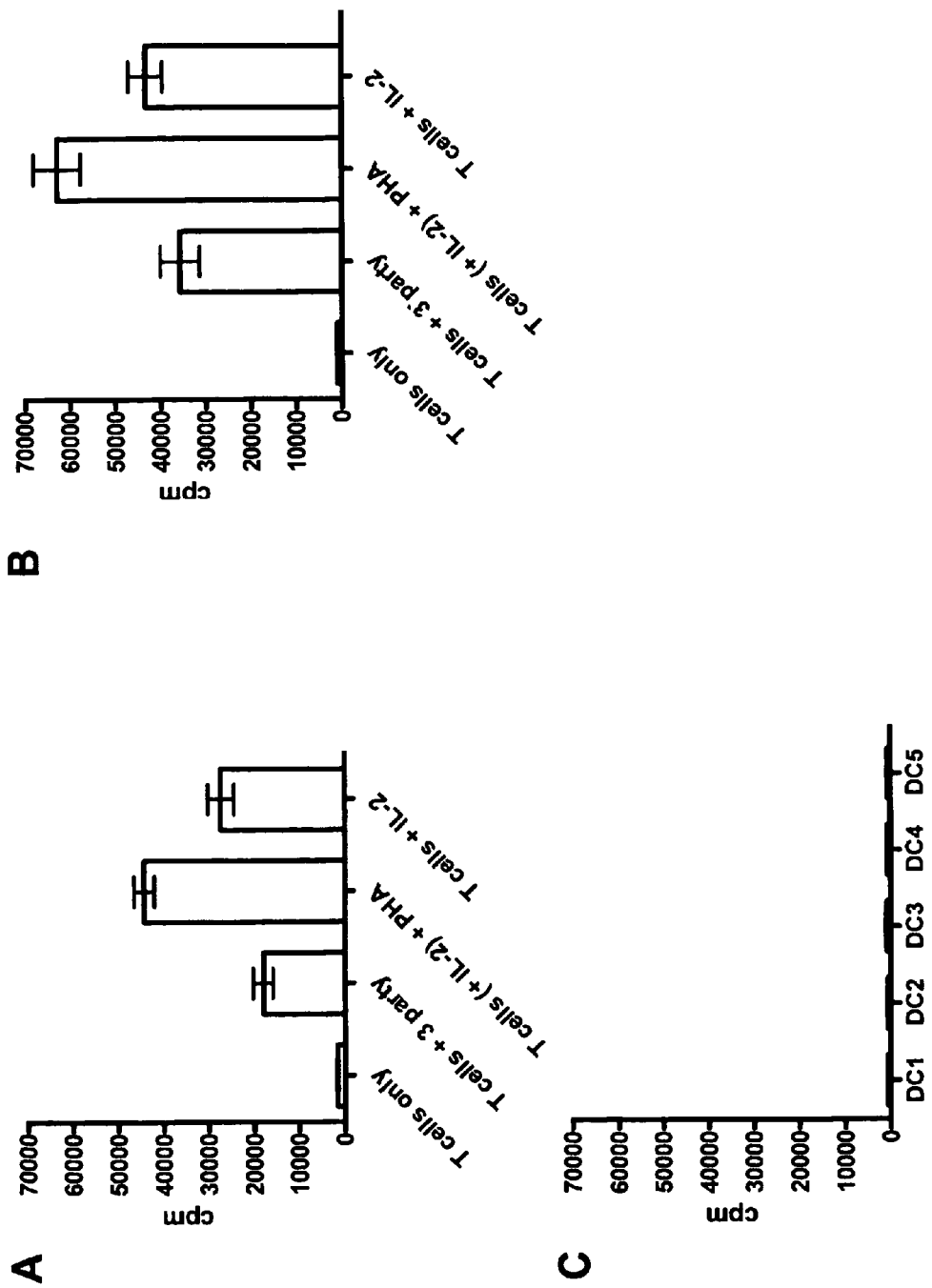
Figure 4/A-C

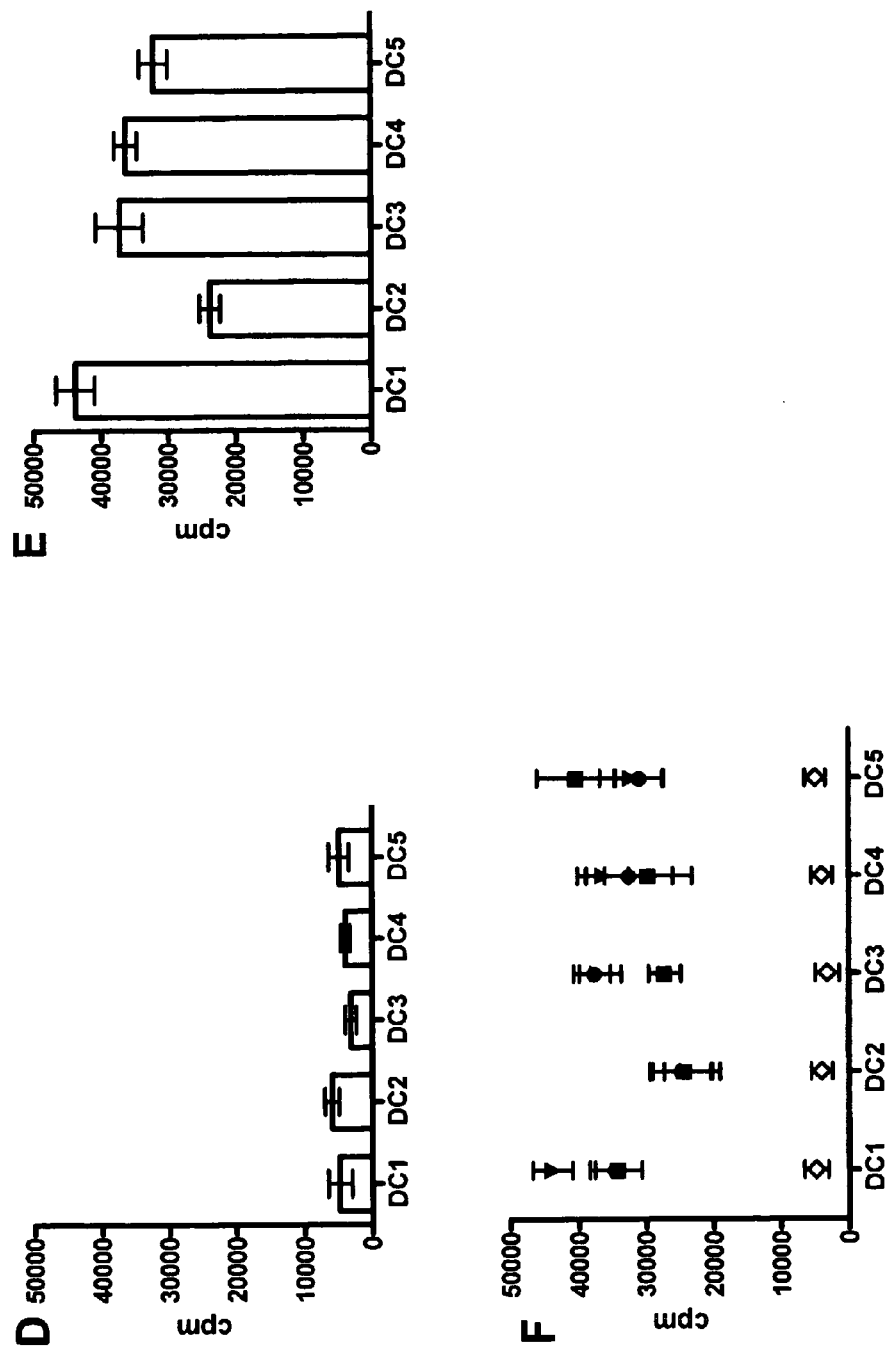
Figure 4/D-F

SEQUENCE LISTING

```
<160> NUMBER OF SEQ ID NOS: 5

<210> SEQ ID NO 1
<211> LENGTH: 9
<212> TYPE: PRT
<213> ORGANISM: Cytomegalovirus

<400> SEQUENCE: 1

Asn Leu Val Pro Met Val Ala Thr Val
1               5

<210> SEQ ID NO 2
<211> LENGTH: 9
<212> TYPE: PRT
<213> ORGANISM: Epstein-Barr Virus

<400> SEQUENCE: 2

Gly Leu Cys Thr Leu Val Ala Met Leu
1               5

<210> SEQ ID NO 3
<211> LENGTH: 9
```

```
-continued

<212> TYPE: PRT
<213> ORGANISM: Influenza A virus

<400> SEQUENCE: 3

Gly Ile Leu Gly Phe Val Phe Thr Leu
1               5

<210> SEQ ID NO 4
<211> LENGTH: 9
<212> TYPE: PRT
<213> ORGANISM: Epstein-Barr Virus

<400> SEQUENCE: 4

Cys Leu Gly Gly Leu Leu Thr Met Val
1               5

<210> SEQ ID NO 5
<211> LENGTH: 9
<212> TYPE: PRT
<213> ORGANISM: Influenza A virus

<400> SEQUENCE: 5

Phe Met Tyr Ser Asp Phe His Phe Ile
1               5
```

COMPOSITIONS FOR THE PREPARATION OF MATURE DENDRITIC CELLS

This application is a national phase application under 35 U.S.C. §371of International Application No. PCT/EP2007/002773 filed Mar. 28, 2007, which claims priority to European Application No. 06006373.2 filed Mar. 28, 2006. This application also claims the benefit of U.S. Provisional Application No. 60/825,822 filed Sept. 19, 2006. The entire text and figures of the above-referenced disclosures are incorporated herein by reference without disclaimer.

The invention relates to novel compositions for the preparation of mature dendritic cells as well as to methods for in vitro maturation of immature dendritic cells and to therapeutic uses of the dendritic cells obtainable by the method of the invention.

Dendritic cells (DCs) have a high potential as adjuvants in the induction of tumor-specific killer and helper cells in the patient (Schuler G, Schuler-Thurner B, Steinman R M. The use of dendritic cells in cancer immunotherapy. Curr Opin Immunol. 2003 April; 15(2): 138-47. Review. Banchereau J, Palucka A K. Dendritic cells as therapeutic vaccines against cancer. Nat Rev Immunol. 2005 April; 5(4):296-306. Review., Salcedo M, Bercovici N, Taylor R, Vereecken P, Massicard S, Duriau D, Vernel-Pauillac F, Boyer A, Baron-Bodo V, Mallard E, Bartholeyns J, Goxe B, Latour N, Leroy S, Prigent D, Martiat P, Sales F, Laporte M, Bruyns C, Romet-Lemonne J L, Abastado J P, Lehmann F, Velu T. Vaccination of melanoma patients using dendritic cells loaded with an allogeneic tumor cell lysate. Cancer Immunol Immunother. 2005 September 27:1-11 [Epub ahead of print]).

For this purpose, mature dendritic cells which have been maturated in vitro from immature dendritic cells derived from the patient, are loaded with tumor-specific antigens and reinjected into the body, preferably next to or in the lymph nodes. Within lymph nodes dendritic cells interact with-naive T cells resulting in active signal transduction during the so called immunological synapse and subsequent proliferation of effector T cells, which, in turn mediate anti tumor responses like cytotoxicity (cytotoxic T lymphocytes=CTLs), activation of macrophages and delayed type hypersensitivity reactions. DCs regulate CD4 positive T helper (h) cell polarizations. Th1 cells, for example, support CTLs by secretion certain cytokine patterns (e.g. Interferon gamma and IL-2, TNF-beta). On the other hand, Th2 cells induce antibodies as well as eosinophiles and degranulation of mast cells by IL-4, IL-5, IL-10 and IL-13 (Langenkamp A, Messi M, Lanzavecchia A, Sallusto F. Kinetics of dendritic cell activation: impact on priming of TH1, TH2 and nonpolarized T cells. Nat Immunol. 2000 October; 1(4):311-6, O'Gara, A: Cytokines induce the development of functionally heterogeneous T helper cell subsets. Immunity 1998, 8: 275-283, Rengarajan J, Szabo S J, Glimcher L H. Transcriptional regulation of Th1/Th2 polarization. Immunol Today. 2000 October; 21(10):479-83. Review).

For the therapy with dendritic cells, it is essential that a sufficient number of major DCs is available. Since, in the patient, only 0.2% of the white blood cells are dendritic cells, it is necessary to have an efficient method for the in vitro production of mature dendritic cells.

In the art, various methods have been proposed for the preparation of mature dendritic cells starting from peripheral blood mononuclear cells, monocytes or other myeloid progenitor cells (Jonuleit H, Kuhn U, Muller G, Steinbrink K, Paragnik L, Schmitt E, Knop J, Enk A H.: Pro-inflammatory cytokines and prostaglandins induce maturation of potent immunostimulatory dendritic cells under fetal calf serum-free conditions. Eur J Immunol. 1997 December; 27(12): 3135-42.), Mosca P J, Hobeika A C, Clay T M, Nair S K, Thomas E K, Morse M A, Lyerly H K. A subset of human monocyte-derived dendritic cells expresses high levels of interleukin-12 in response to combined CD40 ligand and interferon-gamma treatment. Blood. 2000 Nov. 15; 96(10): 3499-504, Mailliard R B, Wankowicz-Kalinska A, Cai Q, Wesa A, Hilkens C M, Kapsenberg M L, Kirkwood J M, Storkus W J, Kalinski P.: alpha-type-1 polarized dendritic cells: a novel immunization tool with optimized CTL-inducing activity. Cancer Res. 2004 Sep. 1; 64(17):5934-7, Napolitani G, Rinaldi A, Bertoni F, Sallusto F, Lanzavecchia A.: Selected Toll-like receptor agonist combinations synergistically trigger a T helper type 1-polarizing program in dendritic cells. Nat Immunol. 2005 August; 6(8):769-76. Epub 2005 Jul. 3. 2005 August; 6(8):769-76.2005, Gautier G, Humbert M, Deauvieau F, Scuiller M, Hiscott J, Bates E , Trinchieri G, Caux C, Garrone P.: A type I interferon autocrine-paracrine loop is involved in Toll-like receptor-induced interleukin-12p70 secretion by dendritic cells. J Exp Med. 2005 May 2; 201(9):1435-46. 2005).

It is accepted that the cultivation of peripheral blood mononuclear cells, monocytes or other myeloid progenitor cells with GM-CSF and either IL-4 or IL-13 results in the production of immature dendritic cells in vitro (Ahn J S, Agrawal B. IL-4 is more effective than IL-13 for in vitro differentiation of dendritic cells from peripheral blood mononuclear cells. Int Immunol. 2005 October; 17(10):1337-46. Epub 2005 Sep. 2.) However, to date, there is no satisfying method available for the maturation of the immature dendritic cells. Jonuleit H. et al. (1997, supra) describe such a maturation process using a composition comprising TNF-α, IL-1, IL-6 and prostaglandin E2 (PG) (the so-called Jonuleit cocktail). Dendritic cells produced by incubation of immature dendritic cells with this composition show the surface markers for mature dendritic cells and can be well harvested. However, these cells fail to produce biological active IL-12p70, which is the most important factor for the induction of Th1 cells in the lymph nodes.

Mailliard, R. et al. describe a composition comprising TNF-α, IL-1, interferon α, interferon γ and polyI:C (Mailliard, R. et al., 2004, supra). In contrast to the above Jonuleit cocktail, incubation of immature dendritic cells with this so called Kalinski cocktail results in mature dendritic cells (as demonstrated by the respective surface markers), which produce IL-12p70. However, these cells are very adherent to the bottom of the culture flasks and are, therefore, nearly impossible to harvest. It is, therefore, very difficult, if not impossible, to obtain sufficient mature dendritic cells for the vaccination therapy with this method.

WO 00/47719 describes a compound (R848) which is proposed for the preparation of mature dendritic cells. In the experiments described in this application, immature dendritic cells are stimulated with R848 only. However, R848 as a single maturation substance is not able to provide all characteristics suitable for clinical dendritic cells. All experiments have been carried out with FCS (fetal calf serum) and, therefore, not applicable under GMP (good manufacturing process) conditions because fetal calf serum-free conditions are crucial for a GMP process.

Therefore, there is still a need for improved methods for the preparation of mature dendritic cells out of immature dendritic cells.

The invention provides a method for in vitro maturation of at least one immature dendritic cell, comprising stimulating said immature dendritic cell with TNF-α, IL-1β, IFNγ, a TLR7/8 agonist and prostaglandin E2 (PG).

The present invention is based on the surprising finding that the combination of TNF-α, IL-1β, IFNγ, a TLR7/8 agonist and prostaglandin E2 (PG) is especially suitable for promoting the in vitro maturation of dendritic cells. Especially, and as demonstrated in the Example, the mature dendritic cells obtained by using said combination surprisingly express IL-12p70 in considerable amounts and are surprisingly easy to harvest, which allows for obtaining mature dendritic cells in considerable amounts. Such mature dendritic cell populations could not be produced with the cocktails known in the art, and especially not with the Jonuleit cocktail or the Kalinski cocktail, as explained above.

Individual techniques for the preparation of mature dendritic cells, e.g. starting from human peripheral blood mononuclear cells, monocytes or other myeloid progenitor cells, and from immature DCs themselves, which have been directly isolated from the blood, are known in the art (Berger T G, Strasser E, Smith R, Carste C, Schuler-Thurner B, Kaempgen E, Schuler G. Efficient elutriation of monocytes within a closed system (Elutra) for clinical-scale generation of dendritic cells. J Immunol Methods. 2005 March; 298(1-2):61-72. Erratum in: J Immunol Methods. 2005 August; 303(1-2):152, Strasser E F, Berger T G, Weisbach V, Zimmermann R, Ringwald J, Schuler-Thurner B, Zingsem J, Eckstein R. Comparison of two apheresis systems for the collection of CD14+ cells intended to be used in dendritic cell culture. Transfusion. 2003 September; 43(9):1309-16. Erratum in: Transfusion. 2003 October; 43(10):1502, Campbell J D, Piechaczek C, Winkels G, Schwambom E, Micheli D, Hennemann S, Schmitz J. Isolation and generation of clinical-grade dendritic cells using the CliniMACS system. Methods Mol Med. 2005; 109:55-70, Dubsky P, Ueno H, Piqueras B, Connolly J, Banchereau J, Palucka A K. Human dendritic cell subsets for vaccination. J Clin Immunol. 2005 November; 25(6):551-72).

Therefore, the basic techniques such as incubation periods, media used, etc., for producing mature dendritic cells out of immature dendritic cells, are known in the art. The present invention relates to a novel combination of factors to be used in the context of these prior art techniques. The method of the present invention can, therefore, be easily practiced by the person skilled in the art, simply by performing prior art methods, but using the above identified combination of factors during the incubation of immature dendritic cells in order to obtain mature dendritic cells.

Furthermore, since each of the individual components has already been individually used in the art, the person skilled in the art can easily determine in which concentration each factor should be used. Additionally, the skilled person would be able to adapt the individual concentration of a given factor depending on compositions of the cell culture medium especially growth factors and serum components.

As a general guidance, TNF-α and IL-1β might be used at concentrations from 1 ng/ml to 50 ng/ml, more preferably from 5 ng/ml to 40 ng/ml, and even more preferably at 10 ng/ml. PG might be used at concentrations from 50 ng/ml to 5000 ng/ml, preferably from 50 ng/ml to 1000 ng/ml, even more preferably from 50 ng/ml to 500 ng/ml or at 100 ng/ml or 250 ng/ml. IFNγ might be used at a concentration between 500 U/ml and 10000 U/ml, preferably between 1000 and 5000 U/ml, and more preferably either at 1000 or 5000 U/ml. Finally, the TLR7/8 agonist, preferably R848, might be used at a concentration between 0.2 and 5 μg/ml, preferably 0.5 μg/ml to 2 μg/ml, more preferably 1 μg/ml.

According to the invention, immature dendritic cells are cultivated with the above combination of factors. This can be performed by adding the factors to the culture medium. Alternatively, the culture medium in which the immature dendritic cells have been grown is replaced by a medium already containing the factors. In a further preferred embodiment, the substances mentioned above are part of a composition added to the culture medium of said immature dendritic cell.

Said culture medium may be of any suitable kind, i.e. it may contain human serum or not, may be supplemented with or without any other animal supplements, like proteins, amino acids, or antibiotics. In a preferred embodiment, the medium is produced and used under GMP conditions.

After the maturation period is completed, DCs may be harvested by up and down pipetting, shaking (by hand or mechanically) and rinsing with salt solution, medium components (e.g. RPMI) or complete medium without cytokines. Cells may be collected, centrifuged and cytokines may be washed out by at least one more resuspension of pelleted DCs.

The immature dendritic cells may further be treated with a TLR3 ligand, preferably polyI:C, e.g. at a concentration of between 10 and 50 ng/ml, preferably 20 ng/ml. TLR3 ligand may be added separately to the cells or may be part of the composition comprising also the other factors.

In a preferred embodiment of the invention, said TLR7/8 agonist is an imidazoquinilone type immune response modifying compound, more preferably 4-amino-2-ethoxymethyl-α, α-dimethyl-1H-imidazol[4,5-c]quinoline-1-ethanol (R848). The production of such compounds is described in detail in WO 00/47719. However, also other TLR7/8 agonists as imiquimod (R837), guanine analog loxoribine, TLR8 agonists as single-stranded RNAs which bind to TLR7/8, e.g. ss polyU and ss RNA40 or combinations of TLR7/8 agonists may be used.

In a further preferred embodiment, the immature dendritic cell used as the starting material of the method of the invention is a monocyte derived immature dendritic cell. Preferably, monocytic progenitors obtained from peripheral blood or leukapheresis and enriched by density gradient centrifugation, elutriation or simply plastic adherence techniques are used.

Alternatively, it is also possible to obtain monocytic progenitor cells from CD34 positive progenitor cells by in vitro differentiation to CD14 positive cells, e.g. with FLT3L, SCF, TPO, Il-3 and/or IL-6.

Preferably, said immature dendritic cell is obtained by incubating human peripheral blood mononuclear cells, monocytes or other myeloid progenitor cells with GM-CSF and IL-4 or IL-13. As already discussed above, corresponding methods are known in the art. Furthermore, such methods are described in the Example.

Any medium suitable for physiological conditioning of mammalian cells e.g. containing standard amino acids, growth factors, carbon source, buffer system, or certain salts may be used. Cell culture may be performed at 37° C. according to medium composition at certain $CO_2$ concentrations.

Furthermore, the immature DC may be obtained directly from peripheral blood e.g. via leukapheresis.

In an especially preferred embodiment, the immature dendritic cell is of human origin, although situations, e.g. scientific research or veterinary medicine applications, may be feasible where immature dendritic cells of mammalian origin may be used.

Consequently, in a further preferred embodiment, the method of the invention comprises the following steps:
  a) preparing mononuclear cells from peripheral blood,
  b) incubating the mononuclear cells of step a) with GM-CSF and IL-4 or IL-13, c) incubating the cells obtained in step b) with a cocktail comprising TNFα, IL-1β, IFNγ, a TLR7/8 agonist, prostaglandin E2 (PG), and, optionally, a TLR3 agonist, preferably polyI:C, and d) harvesting the mature dendritic cell or cells.

In step a), the mononuclear cells may be obtained by leukapheresis from peripheral blood. Furthermore, mononuclear cells may be isolated by magnetic or FACS sorting, elutriation or plastic adherence or density gradient centrifugation (e.g. metricamide)

Preferably, the incubation in step b) takes 1 to 9, preferably 2 to 9, more preferably 2 to 6 days. However, it is also feasible to spare steps a) or b) if using freshly isolated immature DCs from peripheral blood/leukapheresis. Furthermore, it is possible that step b) lasts only hours and may be performed in combination with step c).

The incubation in step c) may take 12 hours to 72 hours, preferably 24 hours or 20 hours.

As already discussed above, the skilled person will be able to adapt these incubation periods, if necessary.

The incubation of the immature dendritic cells and the harvesting have already been described above.

In a further preferred embodiment of the invention, the mature dendritic cell or cells is/are further loaded in vitro with one or more antigens. The loading of the mature cells with said antigens is described below in more detail.

Preferably, said antigen or antigens are supposed to trigger the effector T cell maturation within the lymph nodes.

More preferably, and as also described below, said loading is performed by incubating the mature dendritc cell or cells with at least one peptide of said antigen or by transfecting the dendritic cell or cells with antigen encoding RNA or DNA.

The invention further relates to a mature dendritic cell or population of mature dendritic cells, obtainable by the method of the invention. As discussed above, the mature dendritic cells obtained by the method of the invention produce considerable amounts of IL-12p70 and are easy to harvest. These combined effects were not observed with the Jonuleit or Kalinski cocktail in the experiments presented herein (see Example).

Figure 7:
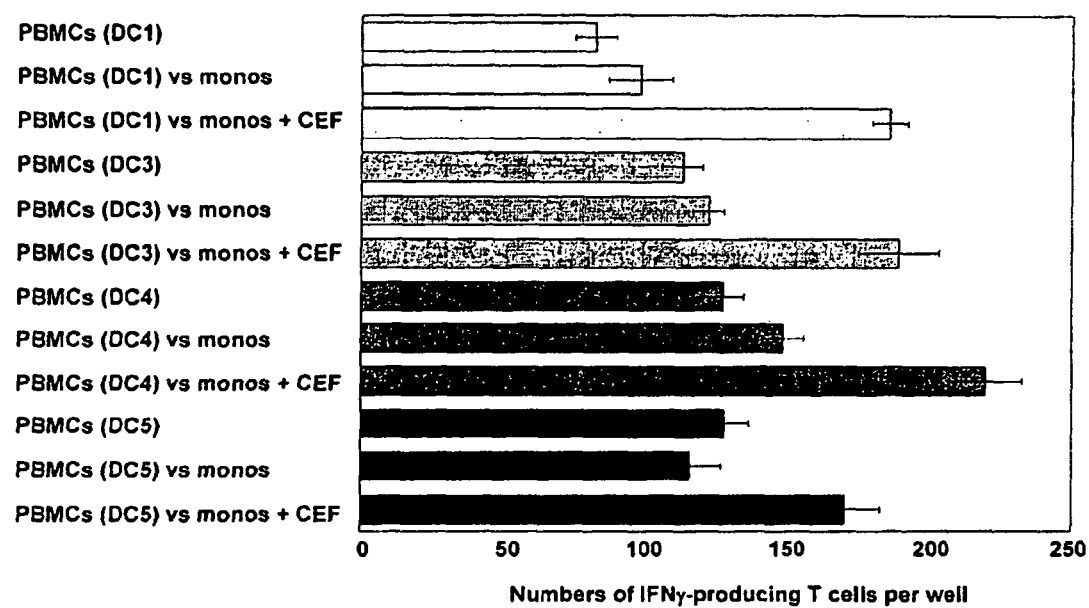
Figure 8:
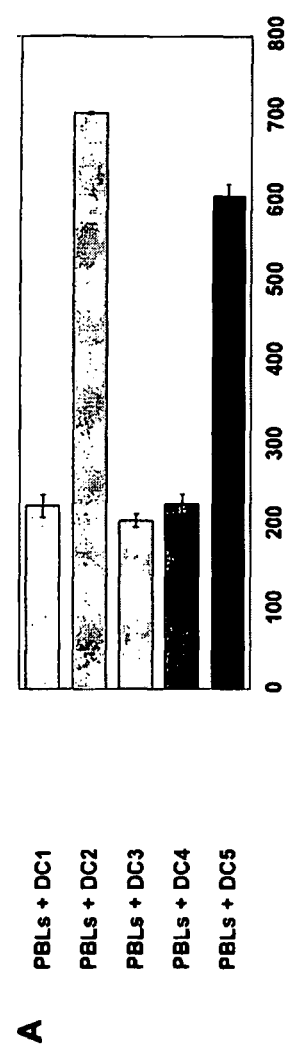

As demonstrated in the Examples and especially in FIGS. 7 and 8, the population of mature dendritic cells of the invention is capable of stimulating interferon-gamma production both of natural killer cells (FIG. 8) as well as of peptide-specific T cells (FIG. 7).

Consequently, the dendritic cells obtainable by the method of the invention are especially suitable in the context of activating T cells in vivo, in order to treat diseases where such activation of T cells is necessary. Consequently, in a further aspect, the present invention also relates to a pharmaceutical composition comprising the mature dendritic cell or the mature dendritic cells. Furthermore, the invention also relates to the use of the mature dendritic cell or of the population of mature dendritic cells of the invention for the preparation of a medicament for the treatment of a disease selected from the group consisting of tumorigenic diseases, and infectious diseases (e.g. provoked by viruses, bacteria, intracellular bacteria or fungi).

In a preferred embodiment, said dendritic cells are obtainable by a method of the invention wherein the cells are incubated also with poly I:C. As indicated above, such dendritic cells are especially capable of stimulating NK cells and are as potent as cells incubated according to the invention without poly I:C in stimulating peptide-specific T cells.

Preferably, for the treatment of the above diseases, the dendritic cells are loaded in vitro with antigens supposed to trigger the effector T cell maturation within the lymph nodes.

Such techniques are known in the art (Dieckmann D, Schultz E S, Ring B, Chames P, Held G, Hoogenboom H R, Schuler G. Optimizing the exogenous antigen loading of monocyte-derived dendritic cells. Int Immunol. 2005 May; 17(5):621-35. Epub 2005 Apr. 11, Kikuchi T, Akasaki Y, Abe T, Fukuda T, Saotome H, Ryan J L, Kufe D W, Ohno T. Vaccination of to glioma patients with fusions of dendritic and glioma cells and recombinant human interleukin 12. J Immunother. 2004 November-December; 27(6):452-9, Gong J, Koido S, Kato Y, Tanaka Y, Chen D, Jonas A, Galinsky I, DeAngelo D, Avigan D, Kufe D, Stone R. Induction of anti-leukemic cytotoxic T lymphocytes by fusion of patient-derived dendritic cells with autologous myeloblasts. Leuk Res. 2004 December; 28(12): 1303-12, Grunebach F, Kayser K, Weck M, Muller M R, Appel S, Brossart P. Cotransfection of dendritic cells with RNA coding for HER-2/neu and 4-1BBL increases the induction of tumor antigen specific cytotoxic T lymphocytes. Cancer Gene Ther. 2005 September; 12(9):749-56, Kyte J A, Kvalheim G, Aamdal S, Saeboe-Larssen S, Gaudernack G. Preclinical full-scale evaluation of dendritic cells transfected with autologous tumor-mRNA for melanoma vaccination. Cancer Gene Ther. 2005 June; 12(6):579-91, Navabi H, Croston D, Hobot J, Clayton A, Zitvogel L, Jasani B, Bailey-Wood R, Wilson K, Tabi Z, Mason M D, Adams M. Preparation of human ovarian cancer ascites-derived exosomes for a clinical trial. Blood Cells Mol Dis. 2005 September-October; 35(2): 149-52, Escudier B, Dorval T, Chaput N, Andre F, Caby M P, Novault S, Flament C, Leboulaire C, Borg C, Amigorena S, Boccaccio C, Bonnerot C, Dhellin O, Movassagh M, Piperno S, Robert C, Serra V, Valente N, Le Pecq J B, Spatz A, Lantz O, Tursz T, Angevin E, Zitvogel L. Vaccination of metastatic melanoma patients with autologous dendritic cell (DC) derived-exosomes: results of the first phase I clinical trial. J Transl Med. 2005 Mar. 2; 3(1): 10, Kawamura K, Kadowaki N, Suzuki R, Udagawa S, Kasaoka S, Utoguchi N, Kitawaki T, Sugimoto N, Okada N, Maruyama K, Uchiyama T. Dendritic cells that endocytosed antigen-containing IgG-liposomes elicit effective antitumor immunity. J Immunother. 2006 March-April; 29(2):165-74, Griffioen M, Borghi M, Schrier P I, Osanto S, Schadendorf D. Analysis of T-cell responses in metastatic melanoma patients vaccinated with dendritic cells pulsed with tumor lysates. Cancer Immunol Immunother. 2004 August; 53(8):715-22. Epub 2004 Mar. 3, Su Z, Dannull J, Yang B K, Dahm P, Coleman D, Yancey D, Sichi S, Niedzwiecki D, Boczkowski D, Gilboa E, Vieweg J. Telomerase mRNA-transfected dendritic cells stimulate antigen-specific CD8+ and CD4+ T cell responses in patients with metastatic prostate cancer. J Immunol. 2005 Mar. 15; 174(6):3798-807).

Loading of dendritic cells with respective antigens could be by competitive displacement of peptides within solutions from the MHC binding groove, or for more complex antigens, like proteins and original tumor lysates or lysates of tumor cell lines, through phagocytosis of immature DCs and proper processing. Transfection methods (lipofection, electroporation or simply incubation of naked nucleic acids) are also feasible and introduce nucleic acids, such as antigen encoding plasmids, RNA of them or DNA and especially RNA from original tumors or tumor cell lines into the DCs. There might also be other antigenic combinations with original MHC molecules conceivable such as membrane fragments or exosomes to use as antigen sources of any kind.

As indicated above, the dendritic cells can be administered directly to the organism to produce T cells active against a selected, e.g. cancerous cell type. Administration of these cells, often with pharmaceutically acceptable carriers, is by any of the routes normally used for introducing a cell into ultimate contact with a mammal's blood or tissue cells.

Formulations suitable for parenteral administration, such as, for example, by intraarticular (in the joints), intravenous, intramuscular, intradermal, intraperitoneal, and subcutaneous routes (preferably intradermal or subcutaneous), and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Intravenous or intraperitoneal administration are the preferred method of administration for dendritic cells of the invention.

The dose of the dendritic cells administered to a patient, in the context of the present invention should be sufficient to effect a beneficial therapeutic response in the patient over time, or to inhibit growth of cancer cells, or to inhibit infection. Thus, cells are administered to a patient in an amount sufficient to elicit an effective CTL response to the virus or tumor antigen and/or to alleviate, reduce, cure or at least partially arrest symptoms and/or complications from the disease or infection. An amount adequate to accomplish this is defined as a "therapeutically effective dose." The dose will be determined by the activity of dendritic cell produced and the condition of the patient, as well as the body weight or surface area of the patient to be treated. The size of the dose also will be determined by the existence, nature, and extent of any adverse side-effects that accompany the administration of a particular cell in a particular patient. In determining the effective amount of the cell to be administered in the treatment or prophylaxis of diseases such as cancer (e.g., metastatic melanoma, prostate cancer, etc.), the physician needs to evaluate circulating plasma levels, CTL toxicity, progression of the disease, and the induction of immune response against any introduced cell type.

Prior to infusion, blood samples are obtained and saved for analysis. Generally at least about $10^4$ to $10^6$ and typically, between $10^8$ and $10^{10}$ cells are infused intravenously or intraperitoneally into a 70 kg patient over roughly 60-120 minutes. Preferably, cell numbers of at least $10^7$/vaccination point are used. The injections may be e.g. 4 times repeated in a 2 weeks interval and should be given preferably near lymph nodes by intradermal or subcutaneous injections. Booster injections may be performed after a 4 weeks pause. Vital signs and oxygen saturation by pulse oximetry are closely monitored. Blood samples are obtained 5 minutes and 1 hour following infusion and saved for analysis. Cell reinfusion are repeated roughly every month for a total of 10-12 treatments in a one year period. After the first treatment, infusions can be performed on a outpatient basis at the discretion of the clinician. If the reinfusion is given as an outpatient, the participant is monitored for at least 4 hours following the therapy.

For administration, cells of the present invention can be administered at a rate determined by the LD-50 (or other measure of toxicity) of the cell type, and the side-effects of the cell type at various concentrations, as applied to the mass and overall health of the patient. Administration can be accomplished via single or divided doses. The cells of this invention can supplement other treatments for a condition by known conventional therapy, including cytotoxic agents, nucleotide analogues and biologic response modifiers. Similarly, biological response modifiers are optionally added for treatment by the dendritic cells. For example, the cells are optionally administered with an adjuvant, a cytokine such as GM-CSF, IL-12, or IL-2, or with KLH.

As indicated above, the invention also relates to the combined use of TNF-α, IL-1β, IFNγ, a TLR7/8 agonist, prostaglandin E2 (PG) and, optionally, a TLR3 agonist, preferably polyI:C for the preparation of at least one mature dendritic cell. Furthermore, the invention also relates to a composition comprising TNF-α, IL-1β, IFNγ, a TLR7/8 agonist, prostaglandin E2 (PG) and, optionally, a TLR3 agonist, preferably polyI:C. As indicated above, in both cases, preferably said TLR7/8 agonist is an imidazoquinilone type immune response modifying compound, preferably 4-amino-2-ethoxymethyl-α,α-dimethyl-1H-imidazol[4,5-c]quinoline-1-ethanol (R848).

The invention will be further described by the following figures and examples, which are not intended to limit the scope of protection as defined in the claims.

SHORT DESCRIPTION OF THE FIGURES

Figure 2:
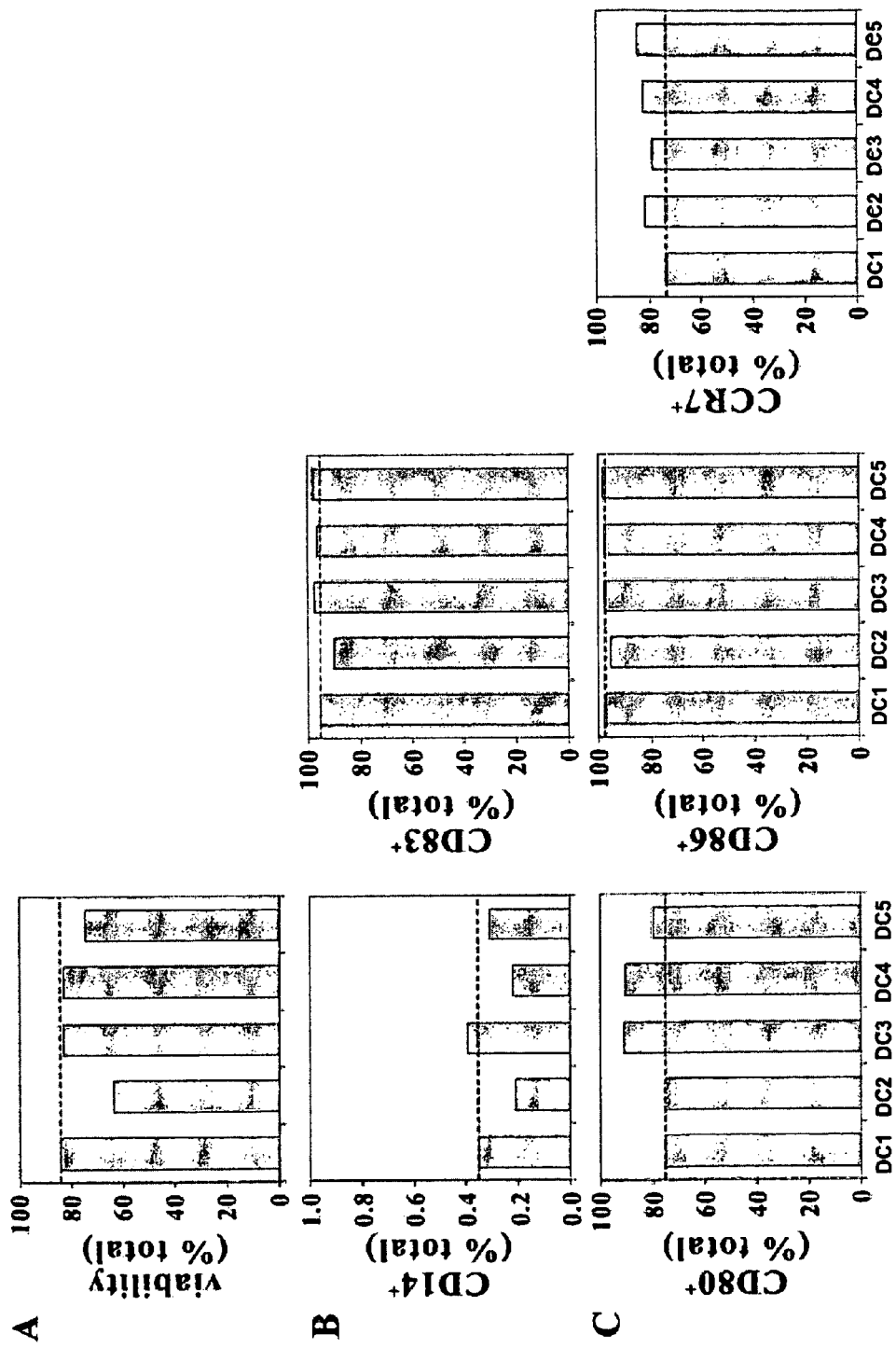

FIG. 1:
Generation of Different Matured Dendritic Cells (DCs)
A. Recovery of harvested DCs after primary cell culture (6 days differentiation+24 h maturation) calculated on seeded total cells (mononuclear cells) or CD14 positive monocytes detected by manual counting within Neubauer chamber and FACS analysis (CD14). Viability detected due to 7AAD incorporation quantitative measured within FL-3 of FACS calibur. Broken line indicated levels of DCs matured with gold standard Jonuleit cocktail.
B. Surface expression of DC specific molecules for DCs after primary DC culture. Low CD14 expression in comparison to high expression of the DC-specific molecule CD83 indicates a mature status of DCs, as detected by FACS analysis (percentage of all cells without gating, aquisition of 10000 cells total).
C. Surface expression of co stimulatory molecules, CD80 and CD86, after primary DC culture detected by FACS analyses. Expression of chemokine receptor 7 (CCR7=CD197) as indication for the migratory potential of DCs into lymph nodes. Positive percentage is detected according to overlay with the isotype control antibody.
DC1=Jonuleit=TNF-alpha (10 ng/ml)+IL-1beta (10 ng/ml)+ IL-6 (15 ng/ml)+Prostaglandin E2 (=PGE2, 1000 ng/ml)
DC2=Kalinski=TNF-alpha (10 ng/ml)+IL-1beta (10 ng/ml)+ IFN alpha (3000 IU/ml)+IFNgamma (1000 IU/ml)+ polyI:C (20 ng/ml)
DC3=TNF-alpha (10 ng/ml)+IL-1beta (10 ng/ml)+PGE2 (100 ng/ml)+IFNgamma (1000 IU/ml)+R848 (1 µg/ml)
DC4=TNF-alpha (10 ng/ml)+IL-1beta (10 ng/ml)+PGE2 (250 ng/ml)+IFNgamma (5000 IU/ml)+R848 (1 µg/ml)
DC5=TNF-alpha (10 ng/ml)+IL-1beta (10 ng/ml)+PGE2 (250 ng/ml)+IFNgamma (5000 IU/ml)+R848(1 µg/ml)+ poly I:C (20 ng/ml)
FIG. 2:
Maturation Stability (Wash Out Test) of Different Matured DCs
DCs were washed out from cytokines and cultured additional 40 h after maturation within DC culture medium with serum and gentamycin only.
A. Viability of different matured DCs after Wash out detected due to 7AAD incorporation.
B. Surface expression of low induced CD14 in comparison to high CD83 expression levels after Wash out.
C. Expression of co stimulatory molecules CD80 and CD86 and CCR7 after Wash out.
DC1=Jonuleit=TNF-alpha (10 ng/ml)+IL-1beta (10 ng/ml)+ IL-6 (15 ng/ml)+Prostaglandin E2 (=PGE2, 1000 ng/ml)

DC2=Kalinski=TNF-alpha (10 ng/ml)+IL-1beta (10 ng/ml)+ IFN alpha (3000 IU/ml)+IFNgamma (1000 IU/ml)+ polyI:C (20 ng/ml)
DC3=TNF-alpha (10 ng/ml)+IL-1beta (10 ng/ml)+PGE2 (100 ng/ml)+IFNgamma (1000 IU/ml)+R848 (1 µg/ml)
DC4=TNF-alpha (10 ng/ml)+IL-1beta (10 ng/ml)+PGE2 (250 ng/ml)+IFNgamma (5000 IU/ml)+R848 (1 µg/ml)
DC5=TNF-alpha (10 ng/ml)+IL-1beta (10 ng/ml)+PGE2 (250 ng/ml)+IFNgamma (5000 IU/ml)+R848 (1 µg/ml)+ poly I:C (20 ng/ml)

FIG. 3:

Cryopreservation of Different Matured DCs.

DCs were frozen and stored under gas phase of liquid nitrogen and analyzed after thawing.

A. Viability of different matured DCs after Wash out detected due to 7AAD incorporation.

B. Low surface expression of CD14 in comparison to high CD83 expression levels after freezing.

C. Expression of co stimulatory molecules CD80 and CD86 and CCR7 after freezing.

DC1=Jonuleit=TNF-alpha (10 ng/ml)+IL-1beta (10 ng/ml)+ IL-6 (15 ng/ml)+Prostaglandin E2 (=PGE2, 1000 ng/ml)
DC2=Kalinski=TNF-alpha (10 ng/ml)+IL-1beta(10 ng/ml)+ IFN alpha (3000 IU/ml)+IFNgamma (1000 IU/ml)+ polyI:C (20 ng/ml)
DC3=TNF-alpha (10 ng/ml)+IL-1beta (10 ng/ml)+PGE2 (100 ng/ml)+IFNgamma (1000 IU/ml)+R848 (1 µg/ml)
DC4=TNF-alpha (10 ng/ml)+IL-1beta (10 ng/ml)+PGE2 (250 ng/ml)+IFNgamma (5000 IU/ml)+R848 (1 µg/ml)
DC5=TNF-alpha (10 ng/ml)+IL-1beta (10 ng/ml)+PGE2 (250 ng/ml)+IFNgamma (5000 IU/ml)+R848 (1 µg/ml)+ poly I:C (20 ng/ml)

FIG. 4:

Analyses of Allostimulatory Capacity of Different Matured DCs in a Mixed Lymphocyte Reaction.

A. Functional control of proliferative ability of autologeous T cells: T cells within medium only, T cells stimulated with third party (=five mixed MNC donors) (4000 rad irradiated 10e5/well, ratio 1:1 stimulatory cells: responder cells), T-cells+IL-2 (51 U/ml) and PHA 10 µg/ml last 68 h, T cells stimulated with 50 IU/ml IL-2. T cell numbers 10e5/well. Co culture over 7 days, proliferation was measured by 3H-thymidin incorporation of last 24 h. All values are calculated out of five repeated wells.

B. Functional control of proliferative ability of one exemplary allogenic T cell responder.

C. Negative control of proliferation of irradiated (4000 rad) different matured DCs (10e4/well, according to cell number of assay ratio 1:10, DCs: responder cells)

D. Proliferation of autologous T cells stimulated by different matured DCs (DC numbers 10e4/well, T cell numbers 10e5, ratio 1:10, DCs: responder cells)

E. Proliferation of one exemplary, allogenic T cell responder stimulated by different matured DCs (DC numbers 10e4/well, T cell numbers 10e5, ratio 1:10, DCs: responder cells).

F. Summary of proliferation data of three independent T cell responders in comparison to autologous T cells stimulated by different matured DCs DC1=Jonuleit=TNF-alpha (10 ng/ml)+IL-1beta (10 ng/ml)+ IL-6 (15 ng/ml)+Prostaglandin E2 (=PGE2, 1000 ng/ml)
DC2=Kalinski=TNF-alpha (10 ng/ml)+IL-1beta (10 ng/ml)+ IFN alpha (3000 IU/ml)+IFNgamma (1000 IU/ml)+ polyI:C (20 ng/ml)
DC3=TNF-alpha (10 ng/ml)+IL-1beta (10 ng/ml)+PGE2 (100 ng/ml)+IFNgamma (1000 IU/ml)+R848 (1 µg/ml)
DC4=TNF-alpha (10 ng/ml)+IL-1beta (10 ng/ml)+PGE2 (250 ng/ml)+IFNgamma (5000 IU/ml)+R848 (1 µg/ml)
DC5=TNF-alpha (10 ng/ml)+IL-1beta (10 ng/ml)+PGE2 (250 ng/ml)+IFNgamma (5000 IU/ml)+R848 (1 µg/ml)+ poly I:C (20 ng/ml)

FIG. 5.

Production of IL-12p70 and IL-10 by DCs Matured by Using Different Cocktails

Immature DCs were cultured with different maturation cocktails and the amounts of IL-12p70 and IL-10 were determined by standard ELISA. Filled bars indicate IL-12p70 and empty bars IL-10 respectively.

A: Supernatant medium of primary maturation cultures after 7 days;

B: Supernatant medium of cultures of washed, matured DCs and CD40L-transfected fibroblasts following a coculture period of 24 hrs, representing a signal3-assay as described in Material and Methods.

C. The quotients of IL-12p70/IL-10 were determined for the DC populations matured in different cocktails, based on the pg/ml-values of the signal-3 assay.

For calculation it was assumed that IL-12p70 and IL-10 are theoretically equal biological potential. Filled circles indicate a positive quotient between 0 and 3, 5, pointed lines valued sharp differences of DCs matured with Jonuleit or Kalinski cocktail for IL-12p70 secretion.

DC1=Jonuleit=TNF-alpha (10 ng/ml)+IL-1beta (10 ng/ml)+ IL-6 (15 ng/ml)+Prostaglandin E2 (=PGE2, 1000 ng/ml)
DC2=Kalinski=TNF-alpha (10 ng/ml)+IL-1beta (10 ng/ml)+ IFN alpha (3000 IU/ml)+IFNgamma (1000 IU/ml)+ polyI:C (20 ng/ml)
DC3=TNF-alpha (10 ng/ml)+IL-1beta (10 ng/ml)+PGE2 (100 ng/ml)+IFNgamma (1000 IU/ml)+R848 (1 µg/ml)
DC4=TNF-alpha (10 ng/ml)+IL-1beta (10 ng/ml)+PGE2 (250 ng/ml)+IFNgamma (5000 IU/ml)+R848 (1 µg/ml)
DC5=TNF-alpha (10 ng/ml)+IL-1beta (10 ng/ml)+PGE2 (250 ng/ml)+IFNgamma (5000 IU/ml)+R848 (1 µg/ml)+ poly I:C (20 ng/ml)

Figure 6:
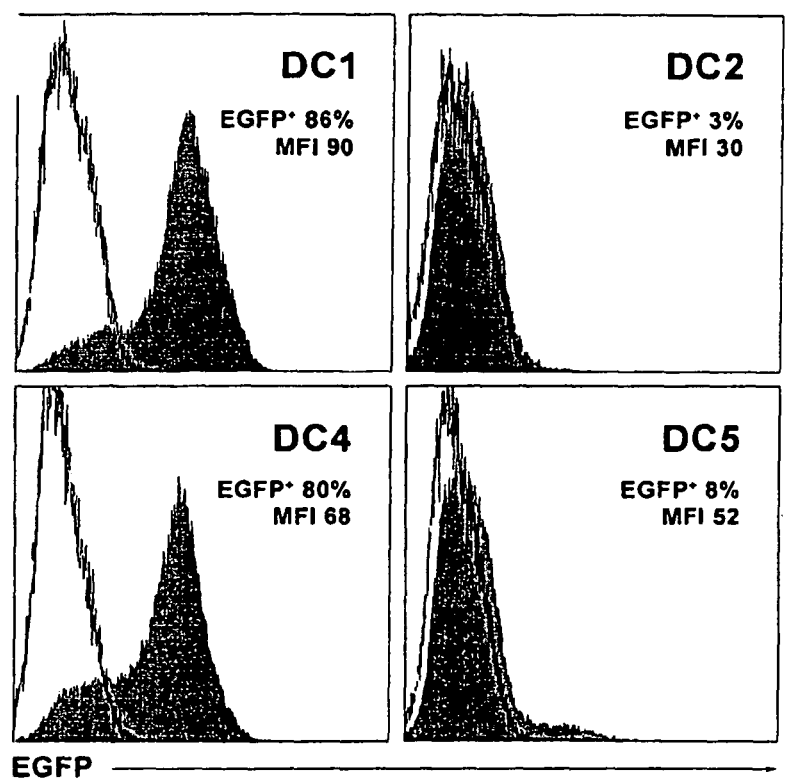

FIG. 6: Expression of EGFP in DCs Transfected with EGFP-Encoding In Vitro Transcribed RNA Flow cytometry histogram overlays show EGFP RNA-transfected into mature DCs (filled curves) 24 h after electroporation and corresponding untransfected DCs (empty curves) as negative controls. DCs were matured in the four cocktails indicated, RNA was introduced by electroporation, the DCs were returned to their corresponding media containing maturation cocktails and harvested for flow cytometry 24 h later. Numbers indicate the percentages of EGFP-positive DCs and their mean fluorescence intensities. These data are representative of two experiments with measurements at 24 and 48 h.

DC1=Jonuleit=TNF-alpha (10 ng/ml)+IL-1beta (10 ng/ml)+ IL-6 (15 ng/ml)+Prostaglandin E2 (=PGE2, 1000 ng/ml)
DC2=Kalinski=TNF-alpha (10 ng/ml)+IL-1beta (10 ng/ml)+ IFN alpha (3000 IU/ml)+IFNgamma (1000 IU/ml)+ polyI:C (20 ng/ml)
DC4=TNF-alpha (10 ng/ml)+IL-1beta (10 ng/ml)+PGE2 (250 ng/ml)+IFNgamma (5000 IU/ml)+R848 (1 µg/ml)
DC5=TNF-alpha (10 ng/ml)+IL-1beta (10 ng/ml)+PGE2 (250 ng/ml)+IFNgamma (5000 IU/ml)+R848 (1 µg/ml)+ poly I:C (20 ng/ml)

FIG. 7: Response of Autologous Lymphocytes from an HLA-A*0201-Positive Donor Responding to Virus-Peptide Pulsed DCs T cell responses were assessed in an IFNγ-ELISPOT experiment using lymphocytes (T cell enriched Elutra fraction 3=54.76% CD3 positive cells) that were first activated for 7 d with mature peptide-pulsed DCs and then restimulated for 24 h with monocytes plus CEF peptides. For the ELISPOT analyses, $4\times10^3$ autologous in vitro activated lymphocytes were stimulated with $2\times10^3$ monocytes together with the five peptide CEF pool. The mean±S.D. was calculated for triplicate wells. Note: Due to insufficient recoveries, lymphocytes activated by DC2 cells were not included in the assay.

DC1=Jonuleit=TNF-alpha (10 ng/ml)+IL-1beta (10 ng/ml)+IL-6 (15 ng/ml)+Prostaglandin E2 (=PGE2, 1000 ng/ml)

DC2=Kalinski=TNF-alpha (10 ng/ml)+IL-1beta (10 ng/ml)+IFN alpha (3000 IU/ml)+IFNgamma (1000 IU/ml)+polyI:C (20 ng/ml)

DC3=TNF-alpha (10 ng/ml)+IL-1beta (10 ng/ml)+PGE2 (100 ng/ml)+IFNgamma (1000 IU/ml)+R848 (1 µg/ml)

DC4=TNF-alpha (10 ng/ml)+IL-1beta (10 ng/ml)+PGE2 (250 ng/ml)+IFNgamma (5000 IU/ml)+R848 (1 µg/ml)

DC5=TNF-alpha (10 ng/ml)+IL-1beta (10 ng/ml)+PGE2 (250 ng/ml)+IFNgamma (5000 IU/ml)+R848 (1 µg/ml)+poly I:C (20 ng/ml)

FIG. 8: Interferon-Gamma Response of Autologous Lymphocytes Stimulated with Mature DCs Lymphocytes from an HLA-A*0201 donor were stimulated with autologous DCs matured using the Jonuleit cocktail, the Kalinski cocktail and the three new cocktails described herein.

Peripheral blood lymphocytes (PBLs) were separated by elutriation and contained in fraction 3, in which 54.8% of the cells were CD3-positive T lymphocytes and 17.7% CD56 positive cells, which is characteristic for natural killer (NK) cells. (A) The elutriation fraction 3 PBLs were directly incubated with the different DC populations matured using the different cocktails and their interferon-gamma secretion (IFN-gamma) was measured after 24 h in a standard ELISPOT assay.

DC1=Jonuleit=TNFα (10 ng/ml)+IL-1β (10 ng/ml)+IL-6 (15 ng/ml)+Prostaglandin E2 (=PGE2; 1000 ng/ml);

DC2=Kalinski=TNFα (10 ng/ml)+IL-1β (10 ng/ml)+IFNα (3000 IU/ml)+IFNγ (1000 IU/ml)+polyI:C (20 ng/ml);

DC3=TNFα (10 ng/ml)+IL-1β (10 ng/ml)+PGE2 (100 ng/ml)+IFNγ (1000 IU/ml)+R848 (1 µg/ml);

DC4=TNFα (10 ng/ml)+IL-1β (10 ng/ml)+PGE2 (250 ng/ml)+IFNγ (5000 IU/ml)+R848 (1 µg/ml);

DC5=TNFα (10 ng/ml)+IL-1 β (10 ng/ml)+PGE2 (250 ng/ml)+IFNγ (5000 IU/ml)+R848 (1 µg/ml)+poly I: C (20 ng/ml).

EXAMPLE

The following example represents the description of one experiment as a representative example of at least three independent experiments performed using different donor cells.

1. Material and Methods

Leukapheresis and Elutriation

To obtain monocytes as a progenitor cell population for generation of human dendritic cells, we used a closed system of elutriation by ELUTRA (Gambro BCT, Lakewood, USA). After informed consent, healthy, unmobilized donors underwent 180 minute leukphereses with the COBE Spectra cell separator (Gambro BCT, Inc. Lakewood, USA.) using a modified MNC program (V6.1): separation factor was set to 700 with a collection rate of 0.8 ml/min and a target hematocrit of only 1-2%. Resulting blood cells were analysed by automatic blood counter ACT Dif (Beckman Coulter, Krefeld, Germany) to set up conditions for ELUTRA system.

Leukapheresis products were processed by ELUTRA (Gambro BCT, Lakewood, USA) according manufacturer's instructions by a method of counter-flow cenrifugal elutriation using a fixed rotor speed (2400 rpm) and computer controlled stepwise adjustment of media flow rate followed by rotor-off harvesting. Therefore 5000 ml of running buffer containing HANKs buffered salt solution (Biochrom, Berlin, Germany) with 1% human serum albumin (Octalbine®, Octapharma, Langen, Germany) were prepared. ELUTRA process resulted in five fractions, with enriched monocytes in the rotor-off fraction. Cellular composition of fractions were characterised by automatic blood counter ACT Diff (Beckman Coulter, Krefeld, Germany) and FACS analysis.

FACS-Analysis of ELUTRA Fractions

Cells of original leukapheresis product and all five ELUTRA fractions were incubated for 30 minutes with the following fluorescein isothiocyanate (FITC)-and phycoerythrin (PE) conjugated monoclonal mouse antibodies: IgG isotype controls (clone X-40), anti-CD14-FITC (clone: MΦP9), anti-CD19-FITC (clone: 4G7), anti-HLA-DR-FITC (clone: L243) (BD Biosciences, Heidelberg, Germany) and anti-CD3-PE (clone UCHT1), anti-CD56-PE (C5.9), anti-CD16-PE (clone: DJ130c), and as a additional control CD14-PE (TÜK4) (Dako Diagnostics, Hamburg, Germany) and anti-CD67-FITC (clone: 80H3) (Immunotech, Marseille, France). Cells were washed and resuspended in PBS+2% fetal calf serum (Biochrom, Berlin, Germany). Flow cytometry analysis was performed on a FACS Calibur device using Cellquest Pro software (BD Biosciences, Heidelberg, Germany).

Generation of Immature Monocyte-Derived Dendritic Cells from Elutriated Monocytes Cells from rotor-off fraction or the subsequently named fraction 5 were used directly for DC generation if CD14 positive cells represented over 60% of all cells detected by FACS analysis. Fraction 5 cells were harvested from ELUTRA collecting bag and washed once with PBS+0.5% human serum and seeded at $35\times10^6/175$ cm$^2$ cell culture flask (NUNC, Wiesbaden, Germany) in 35 ml DC medium containing RPMI 1640 with very low endotoxin (Biochrom, Berlin, Germany), 1.5% human serum (pool of AB-positive adult males) (Blood Bank, University of Tuebingen, Germany) and 10 µg/ml Gentamycin (Biochrom, Berlin, Germany) and cultivated for six days by 37° C., 5% $CO_2$ in a humidified atmosphere. At day 1, 3 and 6 cell cultures were supplemented with 100 ng/ml GM-CSF (Leukine® by Berlex, Richmond, USA) and 20 ng/ml recombinant human IL-4 (R&D Systems, Wiesbaden, Germany) in 7 ml fresh DC medium per flask.

Maturation of Dendritic Cells

Maturation processes were induced by adding different combinations of cytokines and other reagents, as indicated, to immature DCs on day 6 along with additional 7 ml fresh DC medium define here per flask:

Jonuleit cocktail: 10 ng/ml TNF-α, 10 ng/ml IL-1-β, 15 ng/ml IL-6 (R&D Systems, Wiesbaden, Germany) and 1 µg/ml prostaglandin E2 (Minprostin®, Pharmacia/Pfizer, Erlangen, Germany), Kalinski cocktail: 10 ng/ml TNF-α, 10 ng/ml IL-1-β (R&D Systems, Wiesbaden, Germany), 3000 IU/ml IFNα (Roferon A®, Roche, Welwyn Garden City, England), 1000 IU/ml IFNγ(ImukinR, Boehringer Ingelheim, Ingelheim, Germany) and 20 ng/ml double-stranded RNA (poly I:C, InVivogen, Toulouse, France).

New cocktail 1: 10 ng/ml TNF-α, 10 ng/ml IL-1-β(R&D Systems, Wiesbaden, Germany), 5000 IU/ml IFNγ (Imukin®, Boehringer Ingelheim, Ingelheim, Germany), 1 µg/ml R848 (InVivogen, Toulouse, France) and 250 ng/ml prostaglandin $E_2$.

As a variation of cocktail 1, we used the same components expect the concentration of IFNγ was reduced to 1000 IU/ml and prostaglandin $E_2$ to 100 ng/ml.

New cocktail 2: similar to cocktail 1 plus 20 ng/ml double-stranded RNA (poly I:C, InVivogen, Toulouse, France).

As a control, one flask received only 7 ml fresh medium only and served as immature DCs (data not shown).

Harvesting of Dendritic Cells

After incubation of DCs with maturation cocktails for 24 h, cells were harvested by washing twice with PBS+0, 5% human serum with light shaking, cells were counted by Neubauer chamber and prepared for the analyses.

Flow Cytometric (FACS)-Analysis

DC Phenotyping:

DCs were labeled with the following fluorescence-conjugated monoclonal mouse antibodies with specificities for isotype controls (clone X-40), CD14 (FITC, MΦP9), CD19 (FITC, clone: 4G7), CD86 (FITC, clone: 2331 FUN-1), CD80 (PE, clone: L307.4) (BD Biosciences, Heidelberg, Germany) and CD209 (PE, clone: DCN46) (Pharmingen, San Diego, USA) and CD3 (FITC, clone: UCHT1), CD56 (FITC, clone: C5.9a), CD1a (FITC, clone: NA1/34) (Dako, Hamburg, Germany) and HLA-DR (PE, clone: B8.12.2, CD40 (PE, clone: mAb89, CD83 (PE, clone: HB15a) (Immunotech, Marseille, France).

CCR7 staining was performed with a rat hybridoma BLR-2 (clone 8E8) (E. Kremmer, GSF) in comparison to isotype control for IgG2a of hybridoma EBNA-A2 (clone R3) by incubation of DCs in culture supernatant for 60 minutes and followed by after washing, and detection with secondary mouse antibody against rat IgG conjugated with cyanin 5 (Jackson Immuno, West Grove, USA).

To test vitality, DCs were pelleted and resuspended for 20 minutes in 7-Aminoactinomycin D (Sigma-Aldrich, Deisenhofen, Germany) at final concentrations of 10 μg/ml in PBS+ 2% fetal calf serum. After washing, cells were analyzed in the third channel of the FACS Calibur machine.

Check of Maturation Stability (WASH OUT Test)

Matured, harvested and washed DCs were reseeded to $2.5-3 \times 10^6/9$ ml fresh DC medium without any cytokines in 25 cm2 cell culture flasks (NUNC, Wiesbaden, Germany). After approximately 44 h, DCs were harvested and phenotyped by FACS analyses.

Signal 3-Assay

DCs were co-cultured with T cell-mimicking cells as described previously (Kalinski, 2004). Briefly, matured, harvested and washed DCs were reseeded in 96 well plates at concentrations of $2 \times 10^4$/well and incubated together with mouse fibroblasts stably transfected with human CD40L Garrone P, Neidhardt E M, Garcia E, Galibert L, van Kooten C, Banchereau J. Fas ligation induces apoptosis of CD40-activated human B lymphocytes. J Exp Med. 1995 Nov. 1; 182 (5):1265-73) at concentrations of $5 \times 10^4$/well. To control proliferation of each cell population alone, DCs with out any additions and CD40L-fibroblasts in standard medium were tested. After 24 h, plates were centrifuged and supernatants of 8 replicate wells were pooled for analyses of IL-10 and IL-12p70 by ELISA.

ELISA (IL-12p70/IL-10)

Secretion of IL-12p70 and IL-10 by DCs during maturation process (primary DCs) and DCs within Signal 3-assay were detected by standard quantitative ELISA. ELISA was performed utilizing pre-tested antibody duo sets for detection of IL-12p70 and IL-10 (R&D Systems, Wiesbaden, Germany) according to manufacturer's instructions. Colorimetric substrate reaction with tetramethylbenzidine and $H_2O_2$ was measured after stopping with $H_3PO_4$ at 450 nm and wavelength correction by 620 nm and analyzed by software easy fit (SLT, Crailsheim, Germany).

Cryopreservation of Dendritic Cells

After harvesting and washing, $20-25 \times 10^6$ dcs were collected in 0.5 ml cold 20% human serum albumin (Octalbine®, Octapharma, Langen, Germany) and gently mixed with 0.5 ml (equal amounts) freshly prepared freezing solution containing 10% glucose (Braun, Melsungen, Germany), 20% DMSO (CryoSURE®, WAK-Chemie, Dessau-Thornau, Germany) in 20% human serum albumin. Cryotubes (NUNC, Wiesbaden, Germany) were stored over night at $-80°$ C. and transferred into the gas phase of a liquid nitrogen container.

Mixed-Lymphocyte Reaction

DCs were matured in vitro as indicated, washed 2 times in PBS+0.5% human serum, irradiated with 40 Gy and plated into 96-well round bottom microplates at $1 \times 10^4$/well (Nunc, Wiesbaden, Germany) in RPMI 1640+1.5% human serum. Cryopreserved cells of fraction 3 after ELUTRA procedure from different donors were used as a source of responder cells and seeded at $1 \times 10^5$/well to the DCs of allogenic donors.

As control for T cell activation via MHC differences third party cells were used as follows: a mixture of MNCs of 5 independent donors obtained from buffy coats after irradication by 40 Gy were used as stimulating cells. General unspecific potential of the T cells to proliferate was controlled by incubation of responder cells with IL-2 (Proleukin® by Chiron, Emeryville, USA) at 50 IU/ml and Phycohaemagglutinin at 10 μg/ml (Sigma-Aldrich, Deisenhofen, Germany).

After 6 days, cells were pulsed with 0.5 μCi/well $^3$H-thymidine (Amersham-Pharmacia, Freiburg, Germany) and uptake of $^3$H-thymidine was determined after 24 h using a β-counter device (Wallac, Freiburg, Germany).

EGFP-RNA Transfection into DCs

EGFP-RNA was produced in vitro and electroporated into mature DCs at 24 h as described previously (Nair, S. K., Boczkowski, D., Morse, M., Cumming, R. I., Lyerly, H. K. and Gilboa, E. (1998). Induction of primary carcinoembryonic antigen (CEA)-specific cytotoxic T lymphocytes in vitro using human dendritic cells transfected with RNA. Nat Biotechnol. 16:364-369, Javorovic, M., Pohla, H., Frankenberger, B., Wolfel, T. and Schendel, D. J. (2005). RNA transfer by electroporation into mature dendritic cells leading to reactivation of effector-memory cytotoxic T lymphocytes: a quantitative analysis. Mol Ther. 12: 734-743), with the exception that each 0.4 cm electroporation cuvette contained a total volume of 300 μl, including 8 μg of EGFP-RNA and $3 \times 10^6$ DCs. After electroporation, DCs were returned to their original maturation media and incubated in a 24-well plate at $37°$ C. and 5% $CO_2$ for 24 or 48 h before flow cytometric analysis.

ELISPOT Assay of Virus-Specific T Cell Activation

For activation, lymphocytes from ELUTRA fraction 3 were plated at $1 \times 10^6$ cells/well with $1 \times 10^5$ viral peptide-loaded DCs in 24-well plates, in RPMI 1640 medium with 10% human serum; 30 IU/ml IL-2 was added at d3 and lymphocytes harvested at d7. HLA-A*0201-binding peptides included: CMVpp65$_{495-503}$ (NLVPMVATV; SEQ ID NO: 1), EBV-BMLF1$_{280-288}$ (GLCTLVAML; SEQ ID NO: 2), influenza M1 protein$_{58-66}$ (GILGFVFTL; SEQ ID NO: 3) or the CEF pool (PANATecs GmbH, Tuebingen, Germany) containing two additional peptides, EBV-LMP-2$_{426-434}$ (CLG-GLLTMV; SEQ ID NO: 4) and influenza RNA polymerase PA$_{46-54}$ (FMYSDFHFI; SEQ ID NO: 5). In vitro activated T cells and autologous monocytes plus CEF peptides were incubated in RPMI 1640 medium containing 2 mM L-glutamine, 1 mM sodium pyruvate, penicillin/streptomycin (100 U/ml), 10% human AB serum (BioWhittaker, Verviers, Belgium) and 20 IU/ml IL-2 at 37° C. with 5% $CO_2$ for 24 h. IFNγ-ELISPOT analysis was performed as described (Becker, C.,et. al. (2001). Adoptive tumor therapy with T lymphocytes enriched through an IFNγ capture assay. Nat Med. 7: 1159-1162, Pohla, H., et al. (2000). Allogeneic vaccination for renal cell carcinoma: Development and monitoring. *Bone Marrow Transplant.* 25: 83-87), with the exception that antibody precoated PVDF plates (Mabtech AB, Nacka, Sweden) and streptavidin-alkaline phosphatase and a ready-to-use BCIP/NBT-plus substrate solution (Mabtech) were used for detection. Spots were counted using the AID reader system ELRO3 with 3.2.3 software (AID Autoimmun Diagnostika GmbH, Strassberg, Germany).

2. Results and Discussion

Primary DC Culture

The ELUTRA fraction 5 of the described example (DC034) contained: 80.6% CD14 positive cells and the following contaminants, 2.89% CD3, 2.2% CD56, 1.47% CD19 and 7.72% CD67-positive cells and was therefore appropriate to generate dendritic cells.

The highest recovery of dendritic cells, based on total seeded cells as well as monocytes (CD14 positive cells), was found using the Jonuleit cocktail, while the lowest was found using the Kalinski cocktail (FIG. 1A). Low cell numbers represent poor ability of to harvest DCs without using cell scrapers or enzymatic digestion. This finding represents a big disadvantage of the Kalinski cocktail in our system which might be due to a higher degree of adherence and fine elongation of dendritic veils of DCs matured with this cocktail. Viability of harvested dendritic cells determined by 7AAD staining showed over 97% live cells using Jonuleit cocktail whereas cells matured with Kalinski cocktail reached only 79.5%, our new cocktails ranged between these two values (FIG. 1A).

The expression of co stimulatory molecules, like CD80 and CD86, reflected the presence of antigen presenting cells, particularly dendritic cells. FIG. 1B shows a high expression level of these molecules in all DCs matured with different cocktails. CD14 is a monocytic molecule, but under the influence of GM-CSF/IL-4 and maturation cocktails it disappears rapidly from the surfaces of dendritic cells. Here we show that DCs generated with all cocktails loose CD14 expression as a clear evidence for a differentiation in the direction of DCs, instead of the also possible differentiation in the direction of macrophages.

CD83 on the other hand serves as the most important marker to indicate the maturation status of DCs. Expression of CD83, in combination with nearly undetectable expression of CD14, demonstrated that in all five matured DC populations, cells were of DC identity and highly mature (FIG. 1B).

The chemokine receptor 7 (CD197) indicates a migratory potential of DCs towards lymph nodes along chemokine gradients of CCL19 and CCL21 within high endothelial venules. All different matured DC populations expressed CCR7 at high levels (FIG. 1C).

DCs after Washing Out Maturation Cytokines (Wash Out-Test)

Stability of maturation status is an important characteristic of clinically applicable DCs, because patients with malignant diseases often show high serum titers of inhibitory cytokines (e.g. IL-10, TGF-beta, IL-6). These cytokines may influence injected DCs by reversing them to an immature status and tolerize a patient's immune system towards vaccinated tumour antigens.

To test if our new cocktails induced stable maturation, we tested important DC marker molecules after washing out all cytokines and incubating the DCs at least 40 h following of re seeding in medium only. Remarkably lower viability was found in DCs matured with the Kalinski cocktail (FIG. 2A). FIG. 2A shows, as we expected, that viability is lost over time, because the DCs are exhausted and cells in such a condition after more than 60 h following incubation with maturation cocktail are not suitable for therapy any longer. For test reasons only we checked surface expression of certain molecules, like re-induction of CD14, which would indicate a reverse to immature DCs. As FIG. 2B shows, the five different matured DCs expressing very low levels (under 1%) of CD14 while retaining high levels of the maturation DC marker CD83. Again DCs matured with Kalinski cocktail, showed slightly lower CD83 values than DCs matured with the other cocktails.

FIG. 2C showed stability of high expression levels of co stimulatory molecules, CD80 and CD86, and of maintenance the migratory potential by CCR7 expression.

DCs after Freezing and Thawing

In this step, we searched for a method for the generation of high number of DCs that are then cryoconserved.

Figure 3:
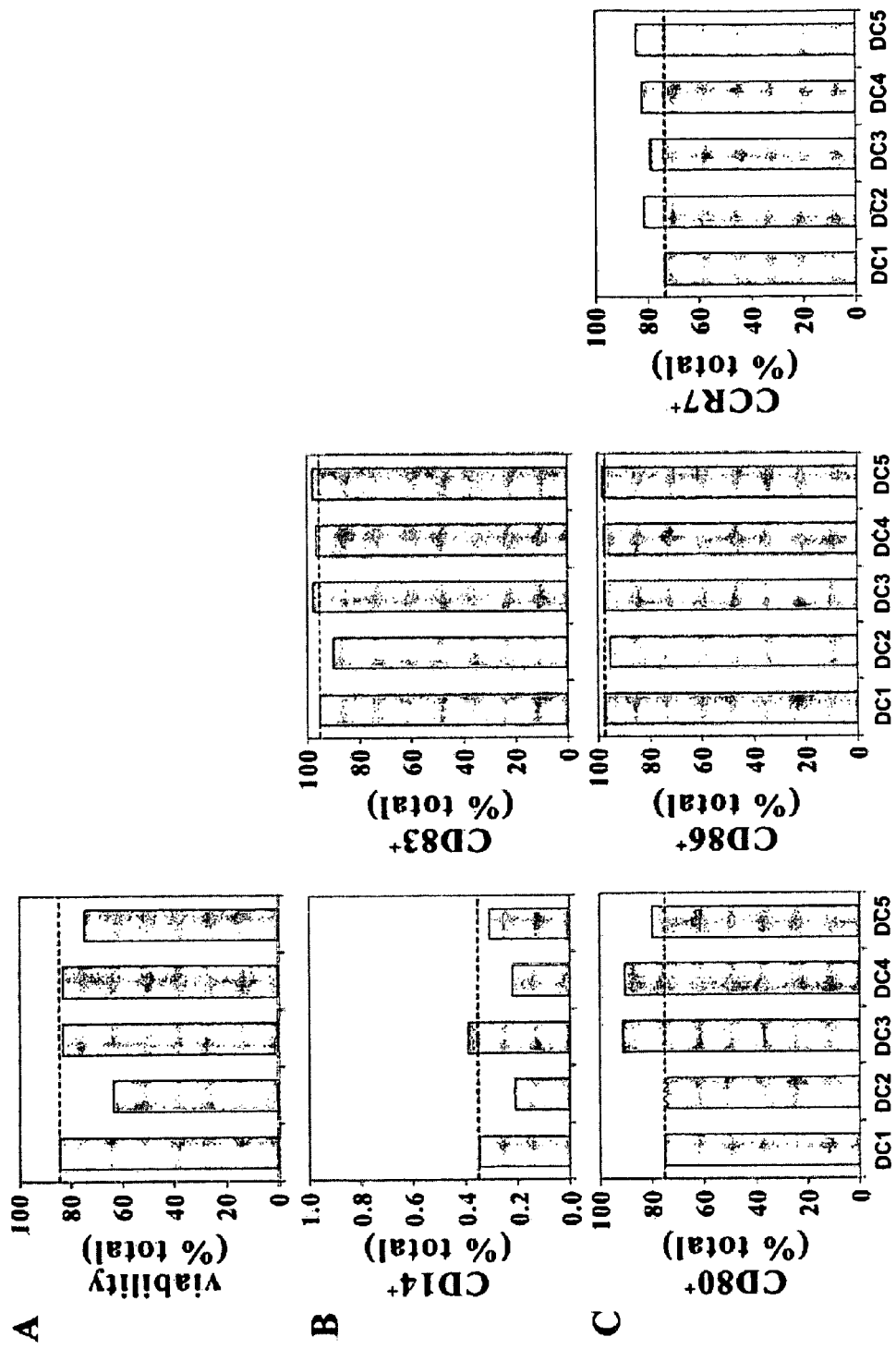

It may be conceivable to freeze monocytes or alternatively, to freeze complete mature DCs, even after antigen loading. FIG. 3 shows viability and maturation markers of the different matured DCs after freezing, storage within the gas phase of liquid nitrogen and the thawing procedure. Viability of over 80% is acceptable, which was obtained by DCs matured with Jonuleit and our new cocktails (FIG. 3A), but not by DCs matured with Kalinski and cocktail 5 (both containing poly I:C). DC markers CD83 and CCR7 were expressed at high levels, and only very low numbers of CD14 cells were detected in all thawed DC populations (FIGS. 3B and C).

Allostimulatory Capacity of DCs

To test functional capacities of DCs, we used a mixed lymphocyte reaction with DCs as stimulatory cells against allogenic T cells. To control vital abilities of T cells, we tested induction of proliferation against a maximal number of different MHC molecules (third party=5 mixed MNC donors), a mitogenic stimuli (PHA) and the T cell stimulatory cytokine IL-2. FIG. 4 shows these controls for the autologeous T cells (4A) and a exemplary allogenic T cells responder (4B). FIG. 4C shows irradiated DCs without any responder cells and verified that the assay only determined proliferation by responder cells. FIG. 4D indicates low autologeous T cell induction in comparison to one allogenic responder (FIG. 4E).

In FIG. 4F, we summarized proliferation of 3 independent allogenic responder T cells after co-incubation with different matured DCs in comparison to autologeous T cells of the DC donor. As expected from the MHC differences between the 3 respective responder T cells and DCs we see a high stimulatory capacity. Again, DCs matured with Kalinski cocktail failed to show stimulation levels comparable to the other matured DCs, which may be due to lower viability and a higher percentage of dying cells during the assay procedure.

IL-12p70 and IL-10 Release of DCs

Figure 5:
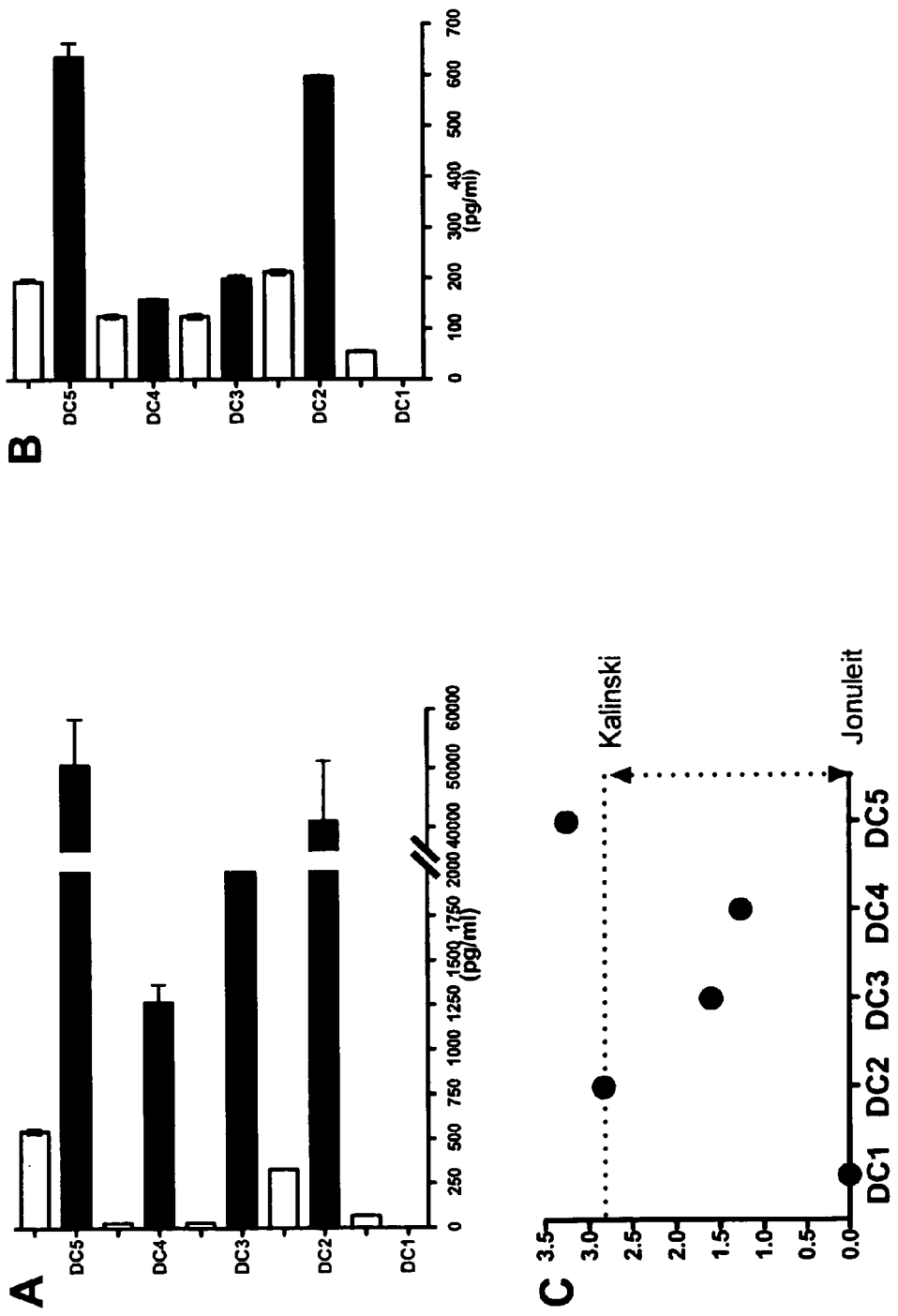

During differentiation and maturation processes, DCs secrete cytokines into their culture supernatant. FIG. 5A shows secretion of biologically active IL-12p70 (filled bars) and IL-10 (empty bars) into primary DC cultures. DCs matured with Jonuleit cocktail do not secrete detectable amounts of IL-12p70, whereas Kalinski cocktail as well as our new cocktails induced IL-12p70 in ng-ranges per ml. These results indicate a composition's capability to induce cytokine production in DCs. In FIG. 5B, it is visible that after mimicking encounter of DCs with potential T cells within lymph nodes via CD40 ligand it is still possible to re-induce IL-12p70 from DCs matured in the Kalinski cocktail and to a lesser degree also using our new cocktails.

IL-10, as a potential Th2 cytokine, counter-regulates Th1 polarization. To take this effect into account, we calculated the values of both of these important regulatory cytokines as having theoretically equal biological potential and determined a quotient of IL-12p70/IL-10. FIG. 5C represents as the results showing that Kalinski cocktail is superior to Jonuleit, as in the literature described, but our new cocktails also revealed positive quotients for IL-12 re-induction after 24 h of CD40 ligation and thereby secrete more IL-12p70 than DCs matured with Jonuleit cocktail.

To summarize the results we disclose herein a new combination of substances, including a TLR7/8 ligand and other cytokines and supplements, which is capable to induce fully maturation of DCs and to induce Th1 regulatory capacities in these cells. In comparison to the DC maturation with Jonuleit cocktail, our cocktails also showed high cell viabilities after harvesting and freezing, high maturation levels by expression of CD83, co stimulatory molecules and migratory potential by CCR7 expression as well as maturation stability. In contrast to Jonuleit cocktail, our cocktail is able to induce IL-12p70 secretion within primary culture as well as after mimicking T cell interaction by CD40 ligation. Mature DCs generated with our new cocktail combine the best characteristics of Jonuleit cocktail in addition to gaining Th1-inducing capacities via IL-12p70. In contrast to the DCs obtained after maturation with the Kalinski cocktail, our new cocktail results in DCs with IL-12p70 secretion without the negative impact of loss of cell numbers and poor caused by extended cell death processes.

Our procedures to generate human dendritic cells are compliant with the regulations of good manufactory practice (GMP) and therefore are useful for clinical application to generate vaccines, which could promote Th1 polarization of effector T cells against tumour antigenic structures.

Expression of Protein Following RNA-Transfer into DCs by Electroporation

Several sources of antigens have been considered for use in DC-based tumor vaccines. RNA is an attractive candidate to provide whole proteins to DCs for processing and presentation, thereby bypassing the need to know specific MHC-binding peptides. To test the capacity of DCs to express protein after loading with in vitro transcribed RNA, we analyzed EGFP expression by flow cytometry after transfer of corresponding RNA. DC3 cells were not included because cocktail 3 was identical to cocktail 4, except for lower amounts of IFNγ and PGE2 (see e.g. legend to FIG. 1). EGFP expression was found previously to peak 12-24 h following RNA transfection into DC1 cells and expression was stable for 48 h (Javorovic, M., Pohla, H., Frankenberger, B., Wolfel, T. and Schendel, D. J. (2005). RNA transfer by electroporation into mature dendritic cells leading to reactivation of effector-memory cytotoxic T lymphocytes: a quantitative analysis. *Mol Ther.* 12: 734-743), therefore, percentages of EGFP-positive cells and mean fluorescence intensities (MFI) were measured 24 and 48 h after electroporation. DC1 and DC4 cells expressed EGFP whereas DC2 cells did not express EGFP and DC5 cells expressed no (FIG. 6) or only very low levels of EGFP (data not shown). This same pattern was seen at 48 h (data not shown). The TLR3 ligand, poly (I:C), was present in Kalinski and cocktail 5 (DC2 and DC5 cells, respectively) but was missing in Jonuleit (DC1 cells) and cocktail 4 (DC4 cells). Kalinski cocktail also contained IFNα, which was not present in any other cocktail. Interestingly, we found elsewhere that DCs matured only with IFNα also failed to express EGFP protein following RNA transfer (Frankenberger, B., et al. (2005). Cell-based vaccines for metastatic renal cell carcinoma: genetically-engineered tumor cells and monocyte-derived dendritic cells. *World J Urol.* 3:166-174).

Induction of IFNγ Secretion by T Cells with Peptide-Pulsed DCs

Because DC5 cells could not be loaded with RNA, their capacity to present peptides was tested as an alternative (FIG. 7). Autologous lymphocytes of ELUTRA fraction 3 of an HLA-A*0201-positive donor were stimulated for 7 days with peptide-pulsed DCs matured in cocktails 3-5 in comparison to Jonuleit cocktail. Cells were then restimulated for 24 h with autologous monocytes plus CEF peptides and analyzed in an IFNγ-ELISPOT assay. Peptide-specific responses were found with all the DC populations, demonstrating that DC5 cells could present peptides for T cell activation.

Therefore, we found that the presence of poly (I:C) in maturation cocktails prevented DCs from being able to express protein after loading with exogenous RNA, presumably through TLR3 activation of mechanisms to protect cells from foreign RNA (Kato, H. et al. (2006). Differential roles of MDA5 and RIG-I helicases in the recognition of RNA viruses. Nature 441: 101-105). Thus, DCs matured in Kalinski medium or cocktail 5 can not be used for RNA-based vaccines, although both are suitable for use with peptides, as shown here for cocktail 5 and published previously for Kalinski cocktail (Mailliard, R. B. et al. (2004). alpha-type-1 polarized dendritic cells: a novel immunization tool with optimized CTL-inducing activity. *Cancer Res.* 64: 5934-5937). In contrast, cocktails 3 and 4 would be well suited for generating IL-12p70-producing DCs using either peptides or RNA as sources of tumor-associated antigens for cancer vaccine development.

Interferon-Gamma Response of Autologous Lymphocytes Stimulated with Mature DCs.

Lymphocytes from an HLA-A*0201 donor were stimulated with autologous DCs matured using the Jonuleit cocktail, the Kalinski cocktail and the three new cocktails described in the patent.

Peripheral blood lymphocytes (PBLs) were separated by elutriation and contained in fraction 3, in which 54.8% of the cells were CD3-positive T lymphocytes and 17.7% CD56 positive cells, which is characteristic for natural killer (NK) cells. The elutriation fraction 3 PBLs were directly incubated with the different DC populations matured using the different cocktails and their interferon-gamma secretion (IFN-gamma) was measured after 24 h in a standard ELISPOT assay.

For ELISPOT analysis, PBLs of ELUTRA fraction 3 were plated in 50 μl per well in triplicates on antibody precoated PVDF plates (Mabtech AB, Nacka, Sweden), following incubation of the plates for 2 h at 37° C. in RPMI 1640 culture medium supplemented with 2 mM L-glutamine, 1 mM sodium pyruvate, penicillin/streptomycin (100 U/ml) and 10% human AB serum (BioWhittaker, Verviers, Belgium) to block unspecific binding. The capture antibody was the IFNγ-specific clone 1-D1K (Mabtech). The DC populations were carefully added to the wells. For background evaluation, DCs and lymphocytes were plated alone. The total culture volume was 150 μl and the plates were incubated in a 37° C. humidified incubator with 5% $CO_2$ for 24 h. After removal of the cells and extensive washing with PBS/0.5% Tween20, incubation with the biotinylated detection antibody, clone 7-B6-1 (Mabtech) and the development of the spots were performed as described previously (1,2), with the exception that strepta-vidin-alkaline phosphatase and a ready-to-use BCIP/NBT-plus substrate solution were used. Spots were counted using the AID reader system ELRO3 with the software version 3.2.3 (AID Autoimmun Diagnostika GmbH, Strassberg, Germany).

For activation, lymphocytes from ELUTRA fraction 3 were plated at $1\times10^6$ cells/well with $1\times10^5$ viral peptide-loaded DCs in 24-well plates, in RPMI 1640 medium with 10% human serum; 30 IU/ml IL-2 was added at d3 and lymphocytes harvested at d7. HLA-A*0201-binding peptides included: CMVpp65$_{495-503}$ (NLVPMVATV), EBV-BMLF1 $_{280-288}$(GLCTLVAML), influenza M1 protein$_{58-66}$ (GILGFVFTL) or the CEF pool (PANATecs GmbH, Tuebingen, Germany) containing two additional peptides, EBV-LMP-2$_{426-434}$ (CLGGLLTMV) and influenza RNA polymerase PA$_{46-54}$ (FMYSDFHFI). In vitro activated T cells and autologous monocytes with or without CEF peptides were incubated in RPMI 1640 medium containing 2 mM L-glutamine, 1 mM sodium pyruvate, penicillin/streptomycin (100 U/ml), 10% human AB serum (BioWhittaker, Verviers, Belgium) and 20 IU/ml IL-2 at 37° C. with 5% $CO_2$ for 24 h. IFNγ-ELISPOT analysis was performed as described (Becker, C., et. al. (2001). Adoptive tumor therapy with T lymphocytes enriched through an IFNγ capture assay. *Nat Med.* 7: 1159-1162; Pohla, H., et al. (2000). Allogeneic vaccination for renal cell carcinoma: Development and monitoring. *Bone Marrow Transplant.* 25: 83-87), with the exception that antibody precoated PVDF plates (Mabtech AB, Nacka, Sweden) and streptavidin-alkaline phosphatase and a ready-to-use BCIP/NBT-plus substrate solution (Mabtech) were used for detection. Spots were counted using the AID reader system ELRO3 with 3.2.3 software (AID Autoimmun Diagnostika GmbH, Strassberg, Germany).

The dominant interferon-gamma producing cells detected at this early time point (see FIG. 8) are activated NK cells, in contrast to the experiments above, where the responses represent those of peptide-specific T cells stimulated by the DCs during the 7 d activation period (see FIG. 7). This analysis demonstrated that activation of NK cells was about three-fold enhanced using DCs matured in cocktail DC5, compared to cocktails DC1, DC3 and DC4.

Combined, these studies show that the DCs, and particularly those in cocktail 5 are able to activate natural killer cells (FIG. 8) as well as effectively restimulate peptide-specific effector T cells recognizing epitopes derived from cytomegalovirus, Epstein-Barr virus and influenza virus.

3. Summary of the Example

Dendritic cell (DC)-based vaccines often utilize monocyte-derived DCs matured with a cytokine cocktail (Jonuleit) of IL-1β, TNFα, IL-6 and prostaglandin E2 (PG). To obtain DCs that direct T cells to Th1-responses, we sought cocktails yielding DCs that produce biologically active IL-12p70. After elutriation of apheresis products by ELUTRA, we cultured enriched monocytes with GM-CSF and IL-4 for 6 days in GMP-conform medium with human serum. Immature DCs were matured for 24 h with various cocktails, containing TLR7/8 ligands with or without poly I:C and interferon β, PG, IL-1β and TNFα. Matured DCs expressed >80% CD83, CD86, CD80 and HLA-DR, CD40, >60% CD209 (data not shown), <2% CD14, and >60% lymph node homing chemokine receptor CCR7. DCs retained full maturity and expressed typical surface markers after cryopreservation and after washing out cytokines and reculture for 44 h.

IL-12p70 and IL-10 were present in supernatants of DCs matured with cocktails containing TLR7/8 ligands. A cocktail of IFNγ, IL-1β, TNFα, PG and the TLR7/8 ligand R848 yielded DCs that secreted IL-12p70 after harvest and 24 h coculture with CD40L-transfected fibroblasts, mimicking encounter with T cells in lymph nodes. We calculated the relative amounts of IL-12p70 versus IL-10 and found that our DCs revealed only a slightly lower quotient of IL-12 to IL-10 as reported by Kalinski (IL-1β, TNFα, IFNα, IFNβ, poly I:C).

Functionality of DCs matured with our new cocktails was tested by mixed lymphocyte culture and ELISpot assays. Our DCs induced alloresponses and stimulated T cells specific for viral antigens comparable to DCs generated by Jonuleit cocktail (data not shown).

In summary, this new cocktail for DC maturation combines characteristics of good harvesting, reasonable recoveries, stability of maturation markers and Th1-inducing capacity with GMP-procedures required for high quality DC vaccines.

---

The invention claimed is:

1. A method for in vitro maturation of at least one immature dendritic cell, comprising stimulating said immature dendritic cell with a composition comprising TNFα, IL-1β, IFNγ, a TLR7/8 agonist and prostaglandin E2 (PGE2), wherein the composition does not comprise IL-6, to provide a mature dendritic cell that expresses a higher level of IL-12p70 than IL-10.

2. The method of claim 1, wherein the composition further comprises a TLR3 agonist.

3. The method of claim 2, wherein the TLR3 agonist comprises polyI:C.

4. The method of claim 1, wherein said TLR7/8 agonist is a imidazoquinilone type immune response modifying compound.

5. The method of claim 4, wherein said imidazoquinilone type immune response modifying compound is 4-amino-2-ethoxymethyl-α,α-dimethyl-1H-imidazol [4,5-c]quinoline-1-ethanol (R848).

6. The method of claim 1, wherein said immature dendritic cell is a monocyte derived immature dendritic cell.

7. The method of claim 6, wherein said immature dendritic cell is derived from human peripheral blood mononuclear cells, monocytes, other myeloid progenitor cells, or from CD34 positive progenitor cells by in vitro differentiation to CD14 positive cells, or wherein said immature dendritic cell is obtained directly from peripheral blood.

8. The method of claim 1, wherein the immature dendritic cell is obtained by incubating human peripheral blood mononuclear cells, monocytes or other myeloid progenitor cells with GM-CSF and IL-4; or GM-CSF and IL-13.

9. The method of claim 1, wherein the immature dendritic cell is of human origin.

10. The method of claim 1, further defined as comprising the following steps:
 a) preparing mononuclear cells from peripheral blood,
 b) incubating the mononuclear cells of step a) with GM-CSF and IL-4; or GM-CSF and IL-13,
 c) incubating the cells obtained in step b) with a cocktail comprising TNFα, IL-1β, IFNγ, a TLR7/8 agonist, prostaglandin E2 (PG), and
 d) harvesting the mature dendritic cell or cells.

11. The method of claim 10, wherein step (c) further comprises incubating the cells with a TLR3 agonist.

12. The method of claim 11, wherein the TLR3 agonist comprises polyI:C.

13. The method of claim 10, wherein in step a) the mononuclear cells are obtained by leukopheresis from peripheral blood.

14. The method of claim 10, wherein the incubation in step b) takes 1 to 9, 2 to 9, or 2 to 6 days.

15. The method of claim 10, wherein the incubation in step c) takes 12 h to 72 h, 20 h or 24 h.

16. The method of claim 1, wherein the mature dendritic cell or cells is/are further loaded in vitro with one or more antigens.

17. The method of claim 16, wherein said antigen or antigens are supposed to trigger the effector T cell maturation within the lymph nodes.

18. The method of claim 16, wherein said loading is performed by incubating the mature dendritic cell or cells with at least one peptide of said antigen or by transfecting the dendritic cell or cells with antigen encoding RNA or DNA.

* * * * *

UNITED STATES PATENT AND TRADEMARK OFFICE
CERTIFICATE OF CORRECTION

PATENT NO.       : 8,679,840 B2
APPLICATION NO.  : 12/294453
DATED            : March 25, 2014
INVENTOR(S)      : Dolores J. Schendel, Anke Zobywalski and Iris Bigalke It is certified that error appears in the above-identified patent and that said Letters Patent is hereby corrected as shown below:

In title page, item (73) Assignee, delete "Helmholtz Zentrum München Deutsches Forschungszentrym für Gesundheit und Umwelt (Gmbh)" and replace with --Helmholtz Zentrum München Deutsches Forschungszentrum für Gesundheit und Umwelt (GmbH)-- therefor.

In title page, item (56) References Cited - Other Publications, delete the 19th reference on page 1 "Grunebach et al., "Cotransfection of dendtritic cells with RNA coding for HER-2/neu and 4-1BBL increases the induction of tumor antigen specific cytotoxic T lymphocytes," Cancer Gene Ther., 12(9)::749-56, 2005." and replace with --Grunebach et al., "Cotransfection of dendtritic cells with RNA coding for HER-2/neu and 4-1BBL increases the induction of tumor antigen specific cytotoxic T lymphocytes," Cancer Gene Ther., 12(9):749-56, 2005.-- therefor.

In title page, item (56) References Cited - Other Publications, delete the 9th reference on page 2 "Nair et al., "Induction of primary carcinembyronic antigen (CEA)-specific cytotosic T lymphocytes in vitro using human dendritic cells transfected with with RNA," Nat. Biotechnol., 16:364-369, 1998." and replace with --Nair et al., "Induction of primary carcinoembryonic antigen (CEA)-specific cytotoxic T lymphocytes in vitro using human dendritic cells transfected with RNA," Nat. Biotechnol., 16:364-369, 1998.-- therefor.

In the Claims

In claim 10, column 22, line 36, delete "(PG)" and replace with --(PGE2)-- therefor.

Signed and Sealed this
Fifteenth Day of July, 2014

Michelle K. Lee
*Deputy Director of the United States Patent and Trademark Office*